(12) United States Patent
Reach, Jr.

(10) Patent No.: US 9,020,577 B2
(45) Date of Patent: Apr. 28, 2015

(54) SYSTEMS, DEVICES AND METHODS FOR CARTILAGE AND BONE GRAFTING

(75) Inventor: John S. Reach, Jr., Guilford, CT (US)

(73) Assignee: Yale University, New Haven, CT (US)

( * ) Notice: Subject to any disclaimer, the term of this patent is extended or adjusted under 35 U.S.C. 154(b) by 64 days.

(21) Appl. No.: 12/994,870

(22) PCT Filed: May 29, 2009

(86) PCT No.: PCT/US2009/003280
§ 371 (c)(1),
(2), (4) Date: Feb. 8, 2011

(87) PCT Pub. No.: WO2009/154691
PCT Pub. Date: Dec. 23, 2009

(65) Prior Publication Data
US 2011/0125003 A1    May 26, 2011

Related U.S. Application Data

(60) Provisional application No. 61/154,609, filed on Feb. 23, 2009.

(51) Int. Cl.
| | |
|---|---|
| A61B 5/05 | (2006.01) |
| G06F 19/00 | (2011.01) |
| A61F 2/46 | (2006.01) |
| A61B 17/00 | (2006.01) |
| A61B 17/56 | (2006.01) |

(52) U.S. Cl.
CPC .......... G06F 19/3437 (2013.01); A61F 2/4657 (2013.01); G06F 19/322 (2013.01); *A61F 2002/4633* (2013.01); *A61B 2017/00969* (2013.01); *A61B 2017/568* (2013.01)

(58) Field of Classification Search
None
See application file for complete search history.

(56) References Cited

U.S. PATENT DOCUMENTS

| | | | | |
|---|---|---|---|---|
| 5,612,028 | A * | 3/1997 | Sackier et al. | 424/93.7 |
| 5,771,310 | A * | 6/1998 | Vannah | 382/154 |
| 5,782,835 | A * | 7/1998 | Hart et al. | 606/79 |
| 6,110,482 | A * | 8/2000 | Khouri et al. | 424/423 |
| 6,205,411 | B1 * | 3/2001 | DiGioia et al. | 703/11 |
| 6,553,152 | B1 * | 4/2003 | Miller et al. | 382/294 |

(Continued)

FOREIGN PATENT DOCUMENTS

WO    WO 2007/092841 A2    8/2007

OTHER PUBLICATIONS

PCT International Search Report dated Dec. 1, 2009 for PCT/US2009/003280.

(Continued)

*Primary Examiner* — Nicholas Evoy
(74) *Attorney, Agent, or Firm* — McCarter & English, LLP

(57) ABSTRACT

Disclosed are systems, methods, devices and products to identify suitable donor sites for harvesting bone-cartilage grafts and to implant such bone-cartilage grafts. In some embodiments, a method includes providing a computer having access to a donor database, the donor database comprising information on each of a plurality of donor joint sites of the body, receiving first data relating to a defect of a joint of a patient, the defect comprising an area of bone, a portion of which includes at least one of, for example, missing and/or damaged cartilage, and identifying, based on the first data, at least one donor site from the donor database of joints for harvesting a graft of bone and cartilage to repair the defect.

14 Claims, 18 Drawing Sheets

(56) References Cited

U.S. PATENT DOCUMENTS

| | | | |
|---|---|---|---|
| 6,585,647 B1* | 7/2003 | Winder | 600/437 |
| 6,591,581 B2* | 7/2003 | Schmieding | 53/396 |
| 6,754,374 B1* | 6/2004 | Miller et al. | 382/128 |
| 6,786,930 B2* | 9/2004 | Biscup | 623/16.11 |
| 6,799,066 B2* | 9/2004 | Steines et al. | 600/407 |
| 7,184,814 B2* | 2/2007 | Lang et al. | 600/416 |
| 7,239,908 B1* | 7/2007 | Alexander et al. | 600/427 |
| 7,371,260 B2 | 5/2008 | Malinin | |
| 7,468,075 B2* | 12/2008 | Lang et al. | 623/16.11 |
| 7,550,007 B2 | 6/2009 | Malinin | |
| 7,747,306 B2* | 6/2010 | Nycz et al. | 600/407 |
| 7,981,158 B2* | 7/2011 | Fitz et al. | 623/17.16 |
| 7,985,230 B2 | 7/2011 | Gil et al. | |
| 8,337,507 B2* | 12/2012 | Lang et al. | 606/102 |
| 8,398,648 B2 | 3/2013 | Gil et al. | |
| 8,500,740 B2* | 8/2013 | Bojarski et al. | 606/86 R |
| 8,623,026 B2* | 1/2014 | Wong et al. | 606/96 |
| 2003/0064090 A1* | 4/2003 | Khouri et al. | 424/426 |
| 2003/0120276 A1* | 6/2003 | Tallarida et al. | 606/61 |
| 2003/0216669 A1* | 11/2003 | Lang et al. | 600/587 |
| 2004/0117015 A1* | 6/2004 | Biscup | 623/16.11 |
| 2005/0008990 A1* | 1/2005 | Ganz et al. | 433/215 |
| 2005/0089544 A1* | 4/2005 | Khouri et al. | 424/426 |
| 2005/0260176 A1* | 11/2005 | Ayares et al. | 424/93.7 |
| 2007/0135917 A1 | 6/2007 | Malinin | |
| 2007/0135918 A1 | 6/2007 | Malinin | |
| 2007/0198022 A1* | 8/2007 | Lang et al. | 606/88 |
| 2007/0233264 A1* | 10/2007 | Nycz et al. | 623/18.11 |
| 2007/0276224 A1* | 11/2007 | Lang et al. | 600/410 |
| 2008/0097608 A1* | 4/2008 | Nycz et al. | 623/16.11 |
| 2008/0243127 A1* | 10/2008 | Lang et al. | 606/87 |
| 2009/0306676 A1* | 12/2009 | Lang et al. | 606/102 |
| 2010/0298894 A1* | 11/2010 | Bojarski et al. | 606/86 R |
| 2011/0125003 A1* | 5/2011 | Reach | 600/407 |
| 2012/0041446 A1* | 2/2012 | Wong et al. | 606/96 |
| 2014/0276231 A1* | 9/2014 | Wood | 600/587 |

OTHER PUBLICATIONS

PCT International Search Report dated Oct. 29, 2010 for PCT/US2010/042154.

Extended European Search Report from European Application No. 09767004.6 (Publication No. 2304645) dated Feb. 25, 2014.

* cited by examiner

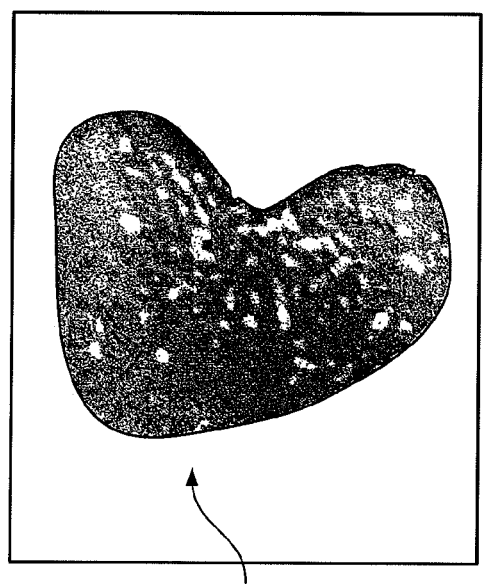
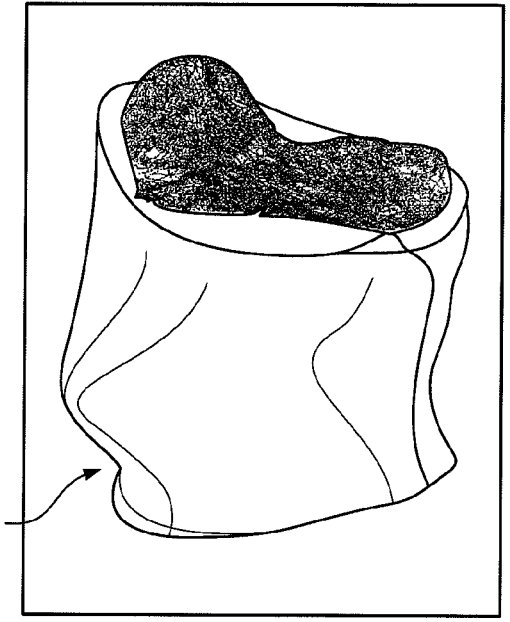
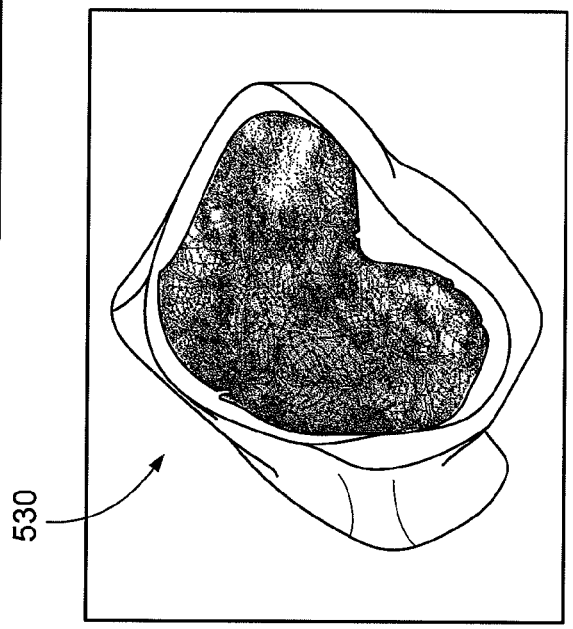
FIG. 8
FIG. 9

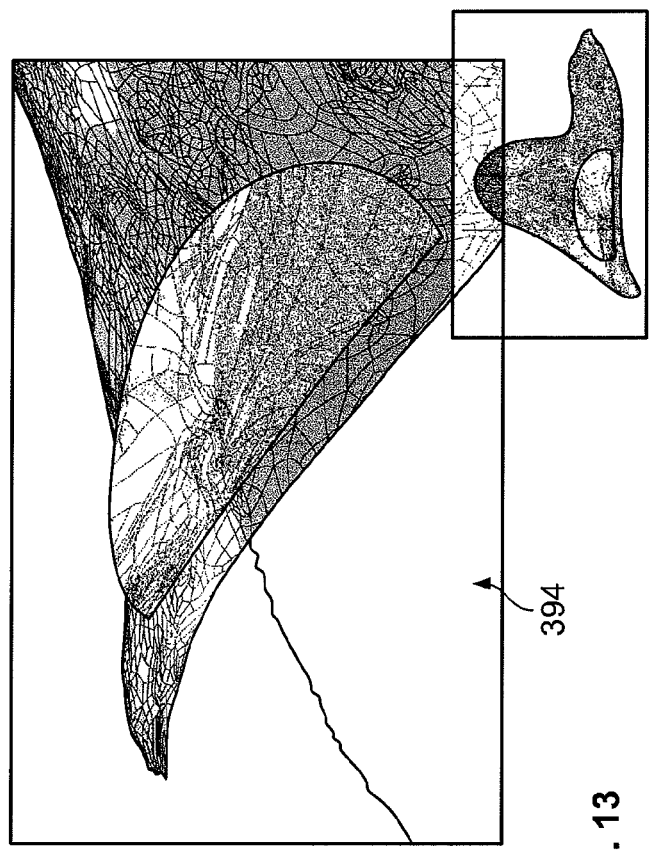
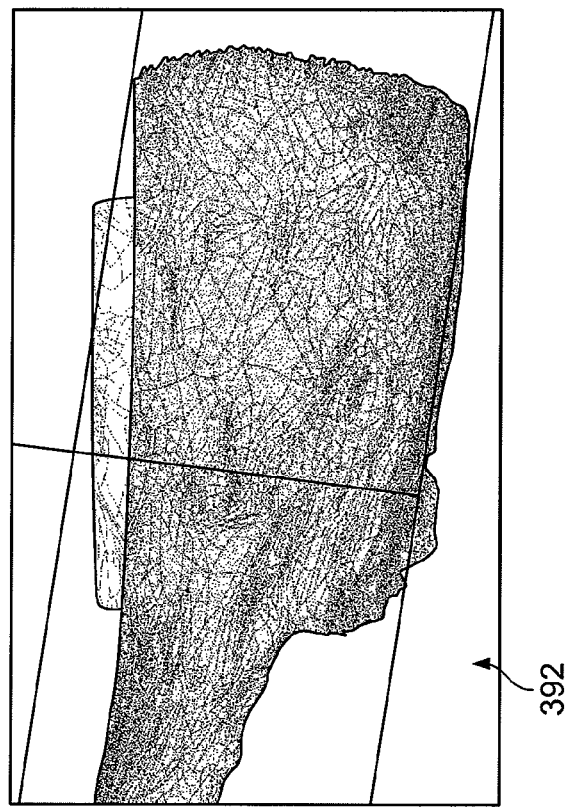
FIG. 13

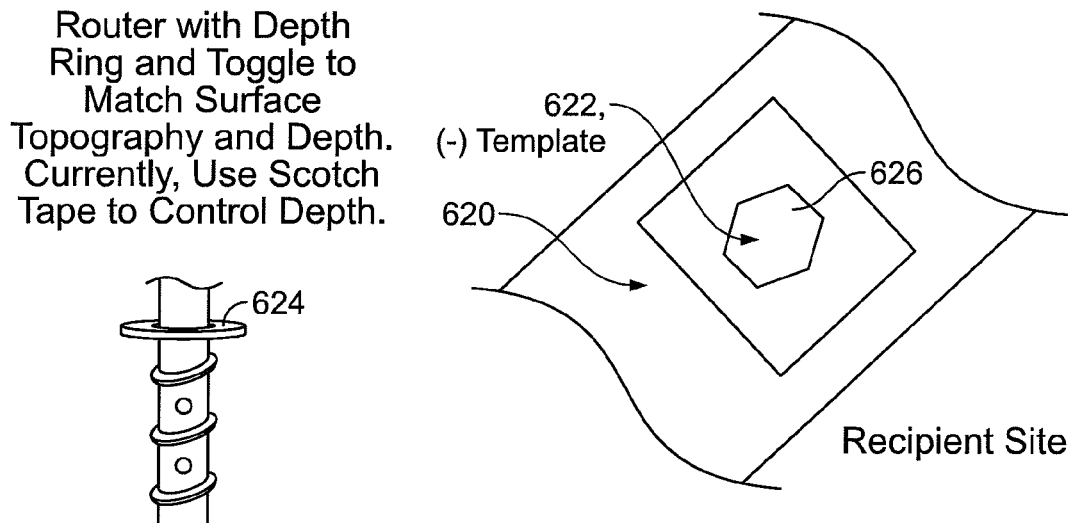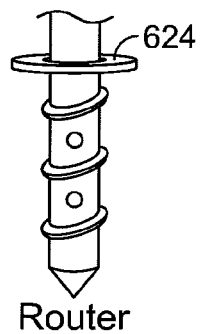
FIG. 16
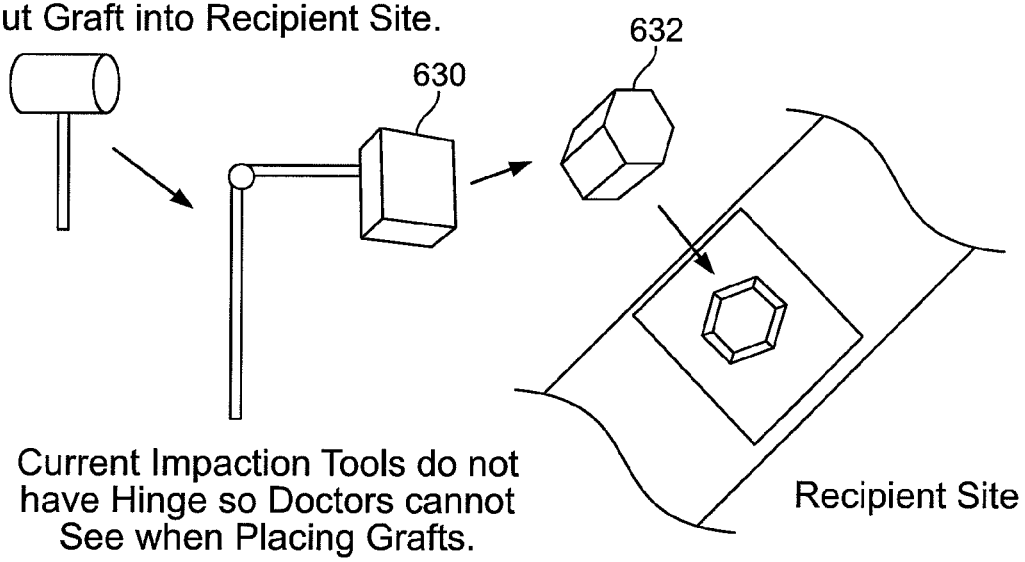
FIG. 17 e.g. 2; Talar Shoulder is Complex Curve
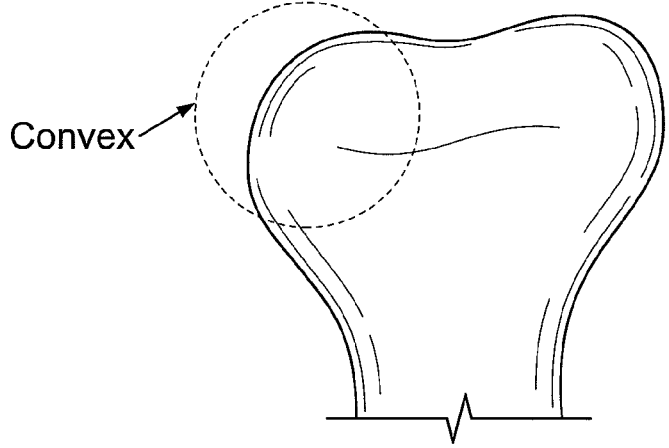
MT Head is Complex Convex Curve
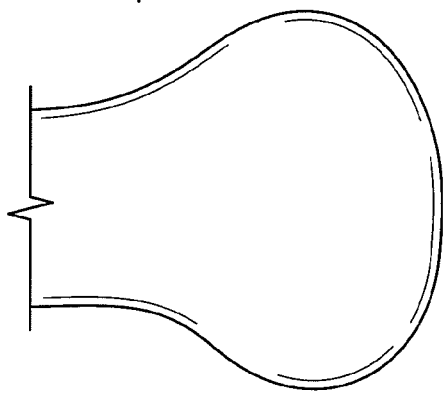
Take Whole Head and Implant into Talus
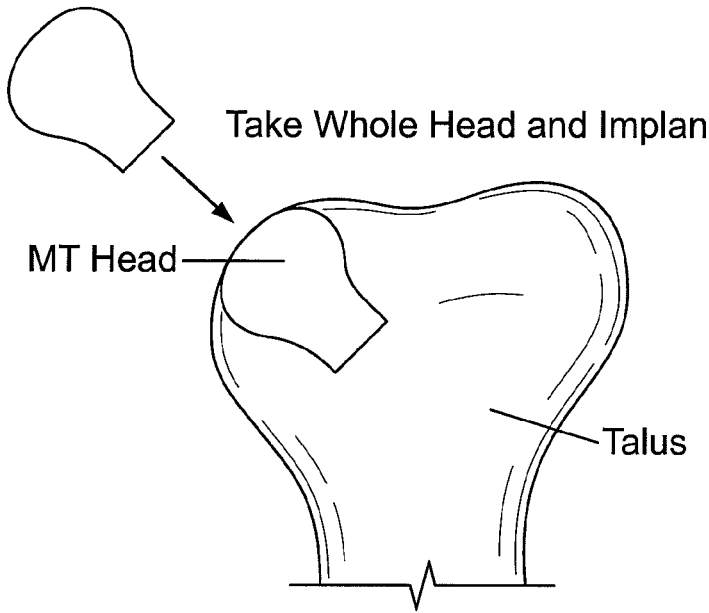
FIG. 25

Central Talus is Complex Concave Curve as is Tibia Plafond
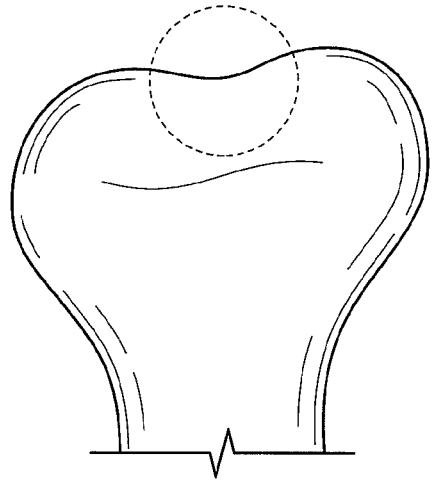
Proximal/Middle/Distal
Phalange Base is Concave
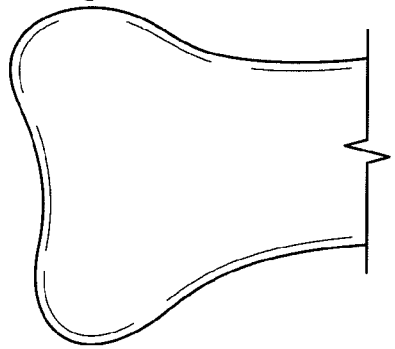
Talar Whole Base with Some of Shape and Implant into Talus/Tibia
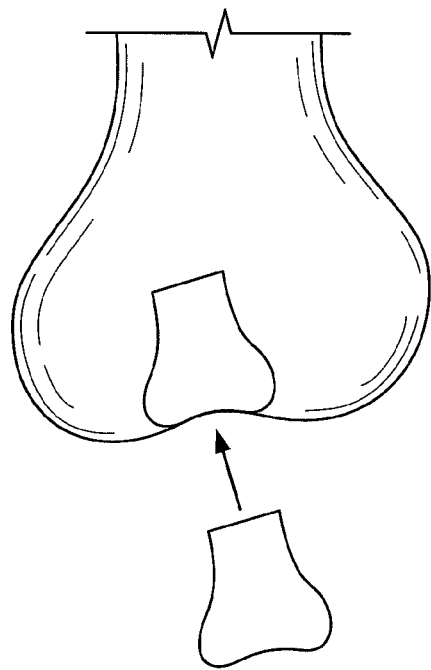
FIG. 26

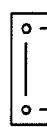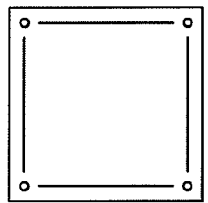
FIG. 27
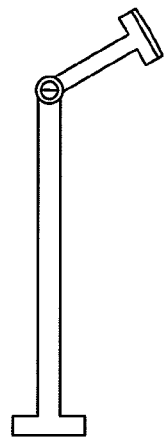
Offset Impacter
FIG. 30
Saw

FIG. 28
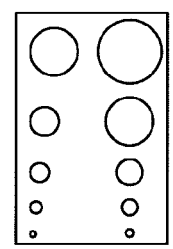
FIG. 31
Routers    Alternate Router
           Concave/Convex
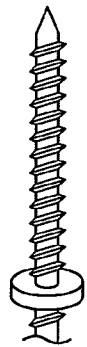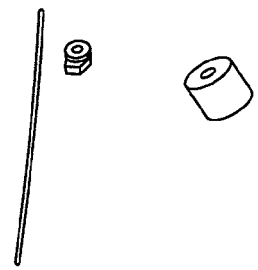
FIG. 29                    FIG. 32

SYSTEMS, DEVICES AND METHODS FOR CARTILAGE AND BONE GRAFTING

CROSS-REFERENCE TO RELATED APPLICATIONS

This application claims priority to provisional U.S. application Ser. No. 61/154,609, entitled "ARTICULAR CARTILAGE GRAFTING DEVICES, METHODS AND SYSTEMS", filed Feb. 23, 2009, the contents of which are hereby incorporated by reference in their entirety.

BACKGROUND

Articular cartilage is a complex structure that, once damaged, has little capacity for permanent repair. The problem lies in the inability of the body to regenerate tissue with the appropriate macromolecular constituents and architecture of normal hyaline cartilage. Although full-thickness defects are capable of stimulating a repair response, the resulting scar tissue or fibrocartilage is inferior and cannot withstand long-term, repetitive use.

To date, no technique has been completely successful in achieving normal degenerative articular cartilage. Arthroscopic lavage and debridement provides temporary relief of symptoms by removing degradative enzymes that contribute to synovitis, but it also leads to the further breakdown of articular cartilage. Bone marrow stimulation techniques such as abrasion arthroplasty, drilling, and microfracture produce only fibrocartilage, and therefore, do not offer a long-term cure. Perichondral and periosteal interposition grafts produce repair tissue that is similar to hyaline cartilage in some respects, but lack its mechanical durability. Like bone marrow stimulation techniques, interposition grafts introduce precursor cells, which have a tendency to differentiate along lines other than cartilage. This leads to an inferior quality of repair tissue.

One technique that provides repair with living hyaline cartilage is osteochondral autograft transplantation, also known as mosaicplasty. This procedure involves removing injured tissue from the damaged area and drilling one or more sockets in the underlying bone. A cylindrical plug graft, consisting of healthy cartilage from the knee is then implanted in each socket. Commercially available instruments for use in this procedure include, Acufex, manufactured by Smith and Nephew, Inc., Andover Mass., COR System, manufactured by Innovasive Technologies, Marlborough Mass., and Arthrex Osteochondral Autograft Transfer System, manufactured by Arthrex, Naples, Fla.

The disadvantages of the current techniques, which harvest cylindrical cores from the knee as grafts, include donor site morbidity, a limited size and supply of grafts, dead space between circular grafts, graft integration and the different mechanical properties and geometry between donor and recipient hyaline cartilage.

SUMMARY

Accordingly, in some embodiments of the present disclosure, an osteochondral autograft transplant system is provided that enables the harvesting of custom osteochondral grafts without the problems associated with the existing systems is provided, and in some embodiments, the grafts being customized relative to at least one of size, shape and depth.

The present disclosure also provides embodiments directed to devices, systems and methods for harvesting custom bone cartilage grafts from anywhere on the body (including in particular from vestigial bones) for transplanting to a recipient site for the correction of a defect/injury (i.e., an area of a joint with damaged cartilage). For example, for an area for which hyaline cartilage is present but which serves little to no function, removal of donor tissue from such joints cause little to no ill effects for the patient. Such areas include, for example, joints of the foot. The foot is an ideal harvest site because many joints in the foot are not used for physiologic motion. In many cases, an entire joint can be sacrificed and then fused with minimal or no loss of motion. Examples of joints of the foot that can be used to harvest grafts include, but are not limited to: the calcanealcuboid joint, the intercuneiform joints, the tarsometatarsal joints, the lesser metatasophalageal joints, and the interphalangeal joints.

These grafts can then be used to repair any cartilage-based joint in the body that requires cartilage-bone transplantation (e.g., articular or hyaline cartilage), including but not limited to, toes, midfoot joints, subtalar, ankle, hip, shoulder, knee, elbow, spinal facet, TMJ, wrist, hand, and finger.

The disclosure further provides a device and method for making custom designed grafts for filling of osteochondral defects throughout the body. By using custom grafts, the disclosed methods, systems, devices and articles eliminate problems associated with an improper fit of the graft in the recipient site, including over-compression or insufficiency of the repair.

In some embodiments, the tools used to create the custom grafts include: a cutting jig with curved surface to match foot topography, a side cutting router with depth ring to control depth, and a press-fit impaction tool with a swivel and lock joint to allow for improved graft insertion.

Some embodiments of the present disclosure include a system for articular/hyaline cartilage repair which includes one or more of the following features:
  determine customized recipient site templates for preparing a recipient site (where the defect is located) for receiving a graft;
  determine a custom jig to harvest bone/cartilage from a donor site;
  determine custom and corresponding harvesting templates (corresponding to the recipient template) for producing a graft for transplantation to the recipient site;
  a computer system and/or network, which utilizes one or more implemented procedures for determining any of the above, as well as:
    determining an appropriate donor site for producing a graft for a particular receiving site, and
    estimating topography of the defect/recipient site.

Some embodiments of the present disclosure include a self-improving system which uses ongoing acquired site-graft data to enhance system precision and accuracy. For example, continued use of such a system provides improved accuracy of the best graft harvesting areas of the body for producing a best topographical match to a patient's defect.

In some embodiments, a defect of a patient is scanned through the use of known imaging systems (e.g., X-ray, CAT scan, MRI, intra-articular ultrasound, and the like). The collected image data is then analyzed by a computer program to select an appropriate sized graft for the defect, and determine where on the patient's body the donor graft can be harvested. While some embodiments of the present disclosure make use of grafts from the patient, embodiments of the present disclosure may include aspects in which grafts taken from other human donors (allografts) as well as from animals (xenograft) can be used. In such cases, selection of donor graft location and template may be determined by one or more procedures (via a computer matching system).

The subject matter of the present disclosure is also directed to generating useful articular joint surface mapping data that can be used to identify harvest sites for optimal or near optimal grafts.

Databases may be utilized by systems (according to some embodiments) for determining the recipient site and donor site templates, as well as suitable locations of donor sites. Such databases may include:
- database of recipient site templates to best match the recipient site and injury pattern;
- database of donor site templates to best match templates compatible with the recipient site; and
- database of locations on a donor body (patient, cadaver, donor, animal) best suited to match the defect (e.g., in terms of topography, cartilage thickness, bone thickness and the like).

In some embodiments of present disclosure, articular/hyaline grafts which constitute a match (sometimes a perfect match) for the defect can be prepared. Such grafts substantially eliminate fibrocartilage growth that results from dead space when, for example, circular grafts are used. In some embodiments, the sites selected to harvest the bone-cartilage grafts are joints located in the feet of an individual (e.g., a patient, another donor, animal donors, etc.). Generally, the feet-based donor sites are joints that are not used, or minimally used by the donor, and thus the harvesting of the bone-cartilage from those locations do not result in an overly detrimental effect on the donor's mobility and/or normal functioning.

At least some of the embodiments of the present disclosure provide computer systems which operate one or more programs implementing procedures for carrying out one or more aspects of the cartilage/bone grafting.

Furthermore, such a system may be configured such that a surgeon can collect the imaging data, and forward it electronically to an application which facilitates determination and selection of the appropriate templates and donor sites. The application which determines and selects such templates and donor sites may be operated as a server or client side application or a stand alone application. Alternatively, the information may be forwarded to a remote location which processes the information and then sends the results to the surgeon. Such procedure may be in the form of tables, or make use of tables, which allow a surgeon to select templates and harvesting sites according to certain predefined criteria. Such tables may include images of the defect for comparative use by the surgeon to compare the defect to that which is provided (by image or otherwise) in such a lookup table, chart, or image catalog.

Accordingly, in some such embodiments, the following operations may be performed.

1) Defect determination/information gathering. The area in and around the defect area is scanned to determine the defect size, shape, and scope. Such information may be gathered by typical imaging technologies (e.g., photo imaged based, x-ray, CAT scan, MRI scanning, ultrasound) and includes collecting imaging information for, in some embodiments, determining the topography of the defect, e.g., contours, cartilage depth, concavity, convex areas, flat areas, and the like, and according to some embodiments, also determining graft harvest locations, templates for both the recipient and donor sites, as well as procedure for any one or more of: recipient site prep, harvest site prep, and the like. In some embodiments, custom grafts may be produced (either locally at the surgical site or at a specific site) via a CNC bone milling machine which takes a donor block of bone/cartilage and produces a custom graft to be received in a custom prepared recipient site. A comparable surgical-recipient site preparation tool/machine/system is also contemplated by the present disclosure, that could be mounted on the patient, and create and/or prepare the recipient site for graft reception.

2) Template determination. Using the imaging information, at least one of the recipient site template and the donor site template are determined. The templates may be complementary of each other (e.g., positive/negative), such that the harvested graft fits within the recipient site. Each set of templates may be customized for a particular patient's defect, in that no two defects are likely to be the same. That being said, other embodiments of the present disclosure include defect repair kits, which include a set number of recipient and donor site templates, which have been found to be applicable to 90% (for example) of all possible defects of joints on a body, or perhaps, all possible defects for a particular joint (e.g., ankle joint). Such kits could be constructed with, for example, a dozen recipient site templates and corresponding harvesting site templates, or some other number which would be applicable to one or several possible defects for, for example, a certain percentage of the population.

3) Harvesting site location. Based on the imaging data, the determined templates, and the topography of the defect (which may also be determined, in some embodiments, if such information is not available from the defect due to the defect's condition), one or more locations having joints with hyaline cartilage with suitable size, structure, thickness, topography (and the like) are selected. Such other information which may also be considered in selecting an appropriate harvesting site includes, for example, the contours (convex, concave, flat areas, etc.).

4) Determining procedure(s). The system may also be able to determine the operation necessary for carrying out either one or more aspects or individual components of the graft transplant procedure, or, the entire procedure.

In one aspect, a method to identify suitable donor sites for bone-cartilage grafts for repairing a defect in a joint of a patient is disclosed. The method includes providing a computer having access to a donor database, the donor database comprising information on each of a plurality of donor joint sites of the body, receiving first data relating to the defect of the joint of the patient, the defect comprising an area of bone, a portion of which includes at least one of, for example, missing and/or damaged cartilage, and identifying, based on the first data, at least one donor site from the donor database of joints for harvesting a graft of bone and cartilage to repair the defect.

Embodiments of the method may include one or more of the following features.

The first data may include imaging data of an area including, for example, at least one of the defect and/or an area around the defect. The first data may include data representative of a surface model of at least one of the defect and/or the area around the defect.

The imaging data may be captured via at least one of, for example, CT imaging, MRI imaging, X-ray imaging and/or laser imaging.

Receiving the first data may include accessing from the donor database data representative of a non-damaged structure corresponding to the defect.

Identifying the at least one donor site may include performing comparisons of data representative of surface models of donor sites retrieved from the donor database to the first data, the first data including data representative of a surface model of at least one of the defect and/or an area around the defect, and determining, based on the comparisons, the at least one donor site. The comparisons may be preformed using the surface model of the at least one of the defect and/or the area around the defect in different spatial orientations.

Performing the comparisons may be performed according to a hierarchy of matching criteria. The matching criteria may include one or more of, for example, a) dimensions of the joint donor sites, the defect and the area around the defect, and/or b) impact of removal from the respective joint donor sites of one or more of cartilage and bone structure.

The method may further include adding to the donor database data relating to one or more joints at donor sites from which bone-cartilage can be removed. Adding to the donor database the data relating to the one or more joints may include capturing an image for each of the one or more joints, and generating a respective surface model for each of the one or more joints at the donor sites based on the respective captured image. The generated respective surface model may include topographical information relating to the respective each of the one or more joint donor sites.

The method may further include overlaying the generated surface model into a model representative of the bone structure associated with cartilage tissue represented by the generated surface model.

Capturing an image for each of the one or more donor joint sites may include disarticulating the each of the one or more donor joint sites on one or more cadavers to expose cartilage tissue at the disarticulated each of the one or more sites, and performing a laser scan of the exposed cartilage to obtain laser-based images of the exposed cartilage.

Providing the computer having access to the donor database may include providing a computer having access to a remotely located database via a communications network.

The at least one donor site from the donor database may include at least one foot joint including, for example, the calcaneal-cuboid joint, intercuneiform joints, arsometatarsal joints, lesser metatasophalageal joints and/or interphalangeal joints.

The method may further include generating a harvesting template based on data relating to the at least one identified donor site.

The method may further include harvesting bone-cartilage from the at least one identified donor site using the generated template. The harvested bone-cartilage may have an irregular shape, the irregular shape including a non-cylindrical shape.

In another aspect, a system to identify suitable donor sites for bone-cartilage grafts for repairing a defect in a joint of a patient is disclosed. The system includes a donor database comprising information on each of a plurality of donor joint sites of the body, the donor database being accessible by a computer. The system further includes a controller processor configured to access the donor database, receive first data relating to the defect of the joint of the patient, the defect comprising an area of bone, a portion of which includes at least one of missing and damaged hyaline cartilage, and identify, based on the first data, at least one donor site from the donor database for harvesting a graft of bone and/or cartilage to repair the defect.

Embodiments of the system may include any of the above described features of the method, as well as one or more of the following features.

The system may further include an imaging apparatus to capture image data of the area including the at least one of, for example, the defect and/or an area around the defect. The controller processor may be further configured to receive the captured image data.

The controller processor configured to identify may be further configured to perform comparisons of data representative of surface models of donor sites retrieved from the donor database to the first data, the first data comprising data representative of a surface model of at least one of the defect and the area around the defect, and determine, based on the comparisons, the at least one donor site.

The at least one donor site from the donor database may include at least one foot joint including, for example, the calcaneal-cuboid joint, intercuneiform joints, arsometatarsal joints, lesser metatasophalageal joints and/or interphalangeal joints.

The system may further include a machine to generate a harvesting template based on data relating to the at least one identified donor site. The machine may include a 3D printer.

The controller processor may be further configured to add to the donor database data relating to one or more joints at donor sites from which bone-cartilage can be removed. The controller processor configured to add to the donor database may be configured to add to the donor database data relating to one or more joint sites using a learning system, the learning system including implementations of one or more of, for example, a neural network, a decision tree and/or a regression procedure.

In a further aspect, a method for bone-cartilage graft implantation is disclosed. The method includes providing a computer having access to a donor database, the donor database comprising information on each of a plurality of donor joint sites of the body, receiving first data relating to a defect of a joint of a patient, the defect including an area of bone, a portion of which includes, for example, at least one of missing and/or damaged cartilage. The method further includes identifying, based on the first data, at least one donor site from the donor database of joints for harvesting at least one graft of bone and cartilage to repair the defect, providing a first at least one template for harvesting the at least one graft of bone and cartilage, the first at least one template positioned at the identified at least one donor site, and providing a second template for removing an area on the joint including the defect, the second template positioned at the defect on the joint.

Embodiments of the method may include any of the features of the above-described first method and the system, as well as one or more of the following features.

The method may further include removing bone-cartilage from the area having the defect using the second template.

The method may further include harvesting the at least one graft of the bone and cartilage using the first at least one template.

The method may further include implanting the at least one graft of bone and cartilage at the area from which the bone-cartilage with the defect was removed.

Harvesting the at least one graft may include harvesting at least one graft having an irregular shape, the irregular shape of the graft including a non-cylindrical graft.

Providing the first at least one template and the second template may include generating at least one of, for example, the first at least one template and/or the second template using a template-generating machine.

Receiving the first data relating to a defect may include receiving image data acquired by one or more of: an MRI imaging apparatus, and a CT imaging apparatus.

Identifying the at least one donor site may include performing comparisons of data representative of surface models of donor sites retrieved from the donor database to the first data, the first data comprising data representative of a surface model of at least one of the defect and an area around the defect, and determining, based on the comparisons, the at least one donor site.

In yet another aspect, a method for bone-cartilage graft implantation is disclosed. The method includes providing a computer having access to a donor database, the donor database comprising information on each of a plurality of donor joint sites of the body, receiving first data relating to a defect of a joint of a patient, the defect comprising an area of bone, a portion of which includes, for example, at least one of missing and/or damaged cartilage. The method further includes identifying, based on the first data, at least one donor site from the donor database of joints for harvesting at least one graft of bone and cartilage to repair the defect, providing a first at least one template for harvesting the at least one graft of bone and cartilage, the first at least one template positioned at the identified at least one donor site, harvesting the at least one graft of bone and cartilage using the first at least one template, preparing an area having the defect to receive the at least one graft of bone and cartilage, and implanting the at least one graft of bone and cartilage at the prepared area.

Embodiments of the method may include any of the features of the above-described first and second methods and the system.

In a further aspect, a computer program product residing on a computer readable medium is disclosed. The computer program product includes computer instructions that when executed on a processor-based device cause the processor-based device to provide access to a donor database, the donor database comprising information on each of a plurality of donor joint sites of the body, receive first data relating to a defect of a joint of a patient, the defect comprising an area of bone, a portion of which includes at least one of, for example, missing and/or damaged hyaline cartilage, and identify, based on the first data, at least one donor site from the donor database of joints for harvesting a graft of bone and cartilage to repair the defect.

Embodiments of the computer program product may include any of the features of the above-described methods and the system.

Details of one or more implementations are set forth in the accompanying drawings and in the description below. Further features, aspects, and advantages will become apparent from the description, the drawings, and the claims.

BRIEF DESCRIPTION OF THE DRAWINGS

FIG. 8 is a diagram of a surface model rendering of a cuboid joint.

FIG. 9 shows generated 3-D representations, in two different orientations, of cartilage surface models overlaid on bone structure models, generated by and for use with at least some embodiments of the present disclosure.

FIG. 13 are two different sectional views of surface models of a donor graft, demonstrating a match with a recipient defect site, as generated by and for use with at least some embodiments of the present disclosure.

FIG. 16 are schematic diagrams of a negative recipient site template placed on a recipient site, and a preparatory tool according to some embodiments of the present disclosure.

FIG. 17 are diagrams of a press-fit impaction tool to insert donor graft according to some embodiments of the present disclosure.

FIG. 25 are diagrams illustrating an example of an articular grafting procedure according to some embodiments of the present disclosure.

FIG. 26 are diagrams illustrating another example of an articular grafting procedure according to some embodiments of the present disclosure.

FIG. 27 are diagrams of harvesting/removal jigs according to some embodiments of the present disclosure.

FIG. 28 are diagrams of various saws according to some embodiments of the present disclosure.

FIG. 29 are diagrams of drill bits and router bits according to some embodiments of the present disclosure.

FIG. 30 is a diagram of an impactor tool according to some embodiments of the present disclosure.

FIG. 31 is a diagram of a sizing chart according to some embodiments of the present disclosure.

FIG. 32 are diagrams of fixation elements according to some embodiments of the present disclosure.

DETAILED DESCRIPTION

Disclosed are systems, methods and article to identify suitable donor sites for bone-cartilage grafts for repairing a defect in a joint in a body of a patient. In some variations, the systems, methods and articles include providing a computer having access to a donor database that comprises information on each of a plurality of donor site joints of the body. A first data (e.g., an image) relating to a defect of a joint of a patient is received (e.g., directly from an imaging apparatus, or from a data repository containing data that may have been earlier processed). The defect with respect to which the first data is received pertains, for example, to an area of a disrupted joint, a portion of which includes at least one of missing and damaged cartilage and bone. Having received the first data, at least one donor site from the donor database of joints is identified, based on the first data, for harvesting a graft of bone and/or cartilage from the at least one site to repair the defect. Some embodiments include an implementation of a learning system that uses acquired site graft data to enhance the precision and accuracy of the system.

Articular cartilage covers the ends of the bones in an articulating joint, and is a white, shiny material with a rubbery consistency. The function of articular cartilage is to absorb shock and provide an extremely smooth bearing surface to facilitate motion. Because it is subject to wear and mechanical shock, areas of articular cartilage may become damaged (e.g., torn or excessively worn) due to injury or disease (e.g., joint dislocation). Damaged areas may be repaired by removing the damaged articular cartilage and implanting healthy cartilage harvested from a donor site, such as a joint of the foot. There are many joints on the human body which may serve as harvest sites for producing hyaline/articular cartilage bone grafts. There are many joints on the human body which may serve as harvest sites for producing hyaline/articular cartilage bone grafts.

In some embodiments of the present disclosure, joints of the foot are utilized as graft areas, since, many joints provided therein are vestigial joints (i.e., not required for the foot to properly function for most if not all activities.)

Figure 1:
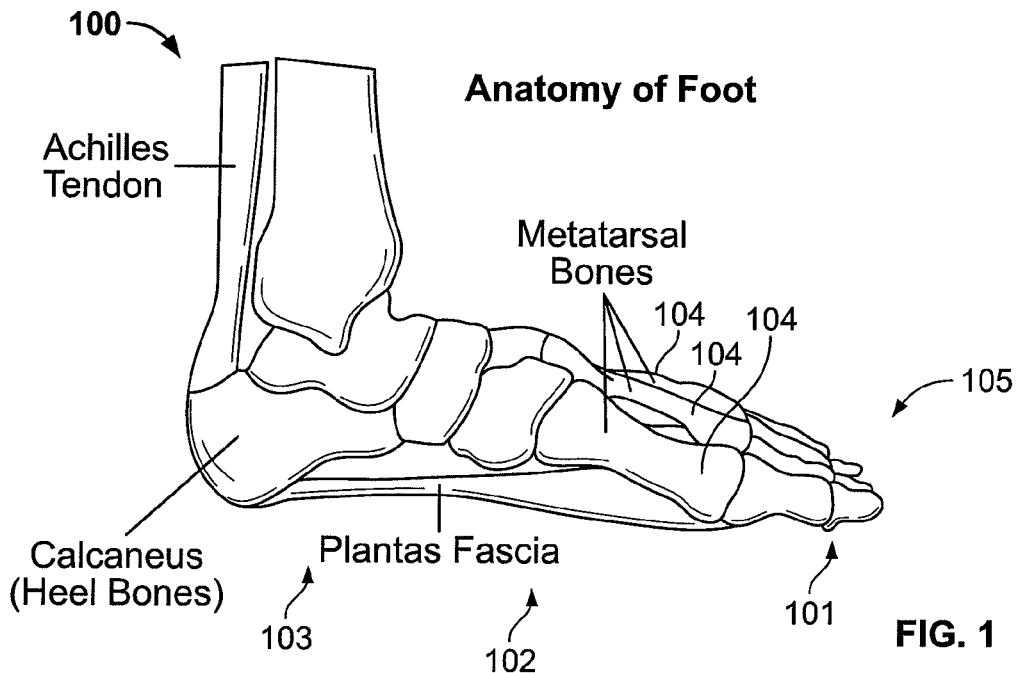
FIG. 1 is a diagram of the anatomy of a foot.
Figure 2:
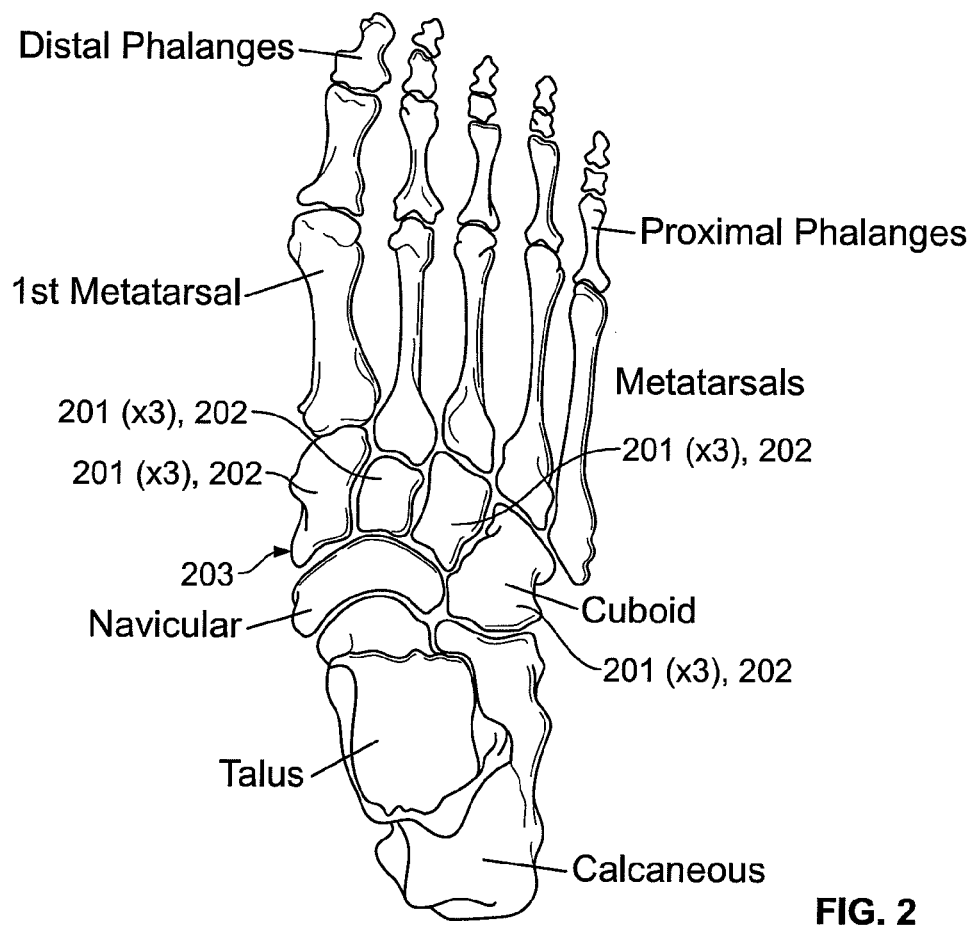
FIG. 2 is another diagram of the anatomy of a foot.

For example, the foot includes a host of possible joints which may be harvested for articular grafts. Referring to FIGS. 1 and 2, a foot 100 is made up of 28 different bones. The foot 100 is divided into three sections: forefoot 101, mid foot 102 and rear foot 103. Fore foot 101 is composed of five metatarsal bones 104, the 14 phalanges that make up toes 105, and at least two sesamoids. The joints between the metatarsals and the proximal phalanx are called metatarsophalangeal joints (MTP). The mid foot 102 includes five tarsal bones, 3 cuneiforms 201, a cuboid 202, and navicular 203. The hind foot and ankle include all the articulations of the talus. In many of these joints, only minor nonphysiologic vestigial motion occurs.

These bones are unique in the way they fit together. A joint describes the predictable geometry which joins these articulations. There are multiple joints among the tarsal bones. The tarsal bones are connected to the five long bones of the foot called the metatarsals. Taken individually and in grouping, these joints are fairly rigidly connected, without much movement. The hind foot 103 consists of the calcaneus (heel bone) and the talus bone, which forms the pivot of the ankle. The talus is connected to the calcaneus at three individual articulations which together comprise the subtalar joint. The talus is almost entirely covered with cartilage and shares articulations with the navicular, cuboid, tibia, and fibula bones.

Examples of joints in the foot that could be used to harvest articular cartilage grafts include, but are not limited to, the calcaneal-cuboid joint, intercuneiform joints, tarsometatarsal joints, lesser metatasophalageal joints and interphalangeal joints.

Identification of Donor Joint Sites to Harvest Bone-Cartilage

Figure 3:
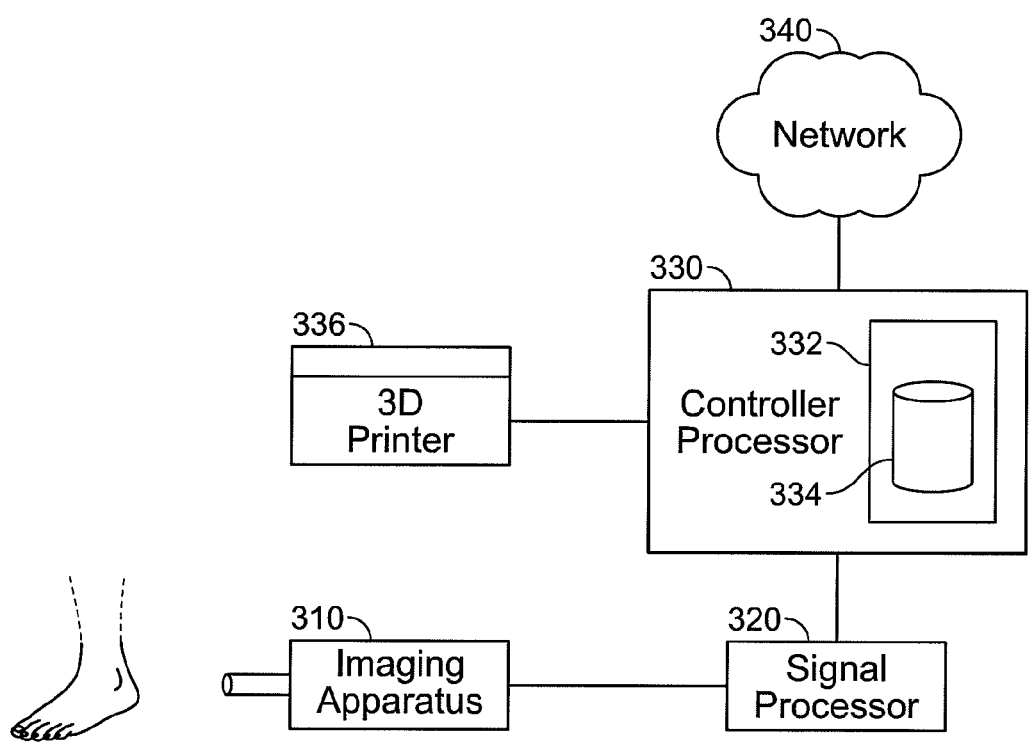
FIG. 3 is a diagram a joint surface mapping system according to some embodiments of the present disclosure.

Referring to now to FIG. 3, a schematic diagram is shown of a joint surface mapping system 300 to acquire data regarding joints (cartilage and bone anatomies) and to enable identification of suitable donor sites to harvest cartilage to repair defects in a patient's bone. The system includes an imaging apparatus 310 to capture image data of an area on a patient's body that includes at least one of the defects and an area around the defect. The imaging apparatus includes, in some implementations, one or more of a Magnetic Resonance Imaging (MRI) system, a computed tomography apparatus configured to generate three-dimensional images from a series of two-dimensional images (e.g., X-Ray) taken around a single axis of rotation, a Medical sonography (ultrasound) imaging device and/or any other suitable imaging device to acquire data representative of anatomical structures in a patient's body. In some embodiments, the data relating to the defect of the joint of the patient may have been acquired at an earlier time and/or at some location other than where the system 300 is located, in which case, the data may be received at the system 300 from some remote location that can electronically communicate (e.g., via one or more types of communication networks such as a network 340, including the Internet, a telephony network, etc.) the data relating to the defect of the joint of the patient.

The imaging apparatus acquires one or more images of a site in the body of a patient that has the defect (e.g., the talus surface at the foot) requiring a cartilage-bone graft procedure to correct. In some embodiments, the mapping system 300 also includes an optional signal processing unit 320 connected to the imaging apparatus 300. The processing unit 320 receives the signals communicated from the imaging apparatus 310 and performs signal processing and/or enhancement operations. Signal enhancement operations may include, for example, amplification, filtering, etc. For example, the processing unit 320 may be configured to perform noise reduction to remove noisy artifacts from acquired image data. Other types of processing may include image processing operations to transform the image data into resultant data that can more easily manipulated for the purpose of identifying donor sites. For example, the acquired data can be processed to generate surface model corresponding to the defect and/or the area proximate the defect, transform spatial representations into another domain (e.g., the frequency domain) that are more conducive for various type of processing, etc.

The processed data can subsequently be communicated to the controller processor 330. The processor includes a storage device 332 to store the data (processed or raw acquired data) relating to the defect of the joint of the patient, and to store a donor database 334 that includes information on each of a plurality of donor site joints of the body. As will become apparent below, the database may be constructed based on data acquired from multiple sources and/or multiple specimens. The acquired data may be used to develop and/or expand the database and enhance the sensitivity and specificity of the system. Typically, the data stored on the database pertains to healthy, non-injured joint specimens (or a composite representation thereof), thus enabling identification of suitable healthy sites in the body from which bone and cartilage can be harvested to perform bone-cartilage grafts. The controller 330 is thus configured to receive a first data relating to a defect of a joint of a patient and to identify, based on that received first data, at least one donor site from the donor database of joints from which it can harvest a graft of bone and cartilage to repair the defect in the patient's joint. In some embodiments, the storage device 332 hosting the donor database 334, or another storage device hosting the database 334, may be located at one or more remote locations that may be accessed by multiple systems such as the mapping system 300. Thus, such a remote device may serve as a central data repository on which data pertaining to donor joint site may be stored. A user locally interacting with the system 300 may therefore access remotely via a network 340 a database such as the database 334 to retrieve data as required. For example, and as will be described in greater details below, data pertaining to potential donor sites that is compared to data relating to an injured joint can be retrieved from that remote location. Optionally, a 3D printer 336 may be locally or remotely interconnected to the controller 330. Such a 3D printer may be used to create 3D custom templates corresponding to any identified donor site and/or to the defect site.

In some implementations, the controller processor may also be configured to perform learning functions. A machine learning system is generally a system that iteratively analyzes training input data and the input data's corresponding output, and derives functions or models that cause subsequent inputs to produce outputs consistent with the machine's learned behavior. Thus, in some embodiments, the controller processor 330 may be configured to perform learning functions that include, for example, identifying the type of donor site corresponding to newly received data, classifying that data so that it is associated with other data sets corresponding to the same anatomical locations, automatically selecting several, potentially suitable, donor sites for further processing with respect to data received regarding the defect site, etc. Some implementations of learning functionalities may be performed using, for example, a neural network system implementation. A neural network includes interconnected processing elements (effectively the systems neurons), whose connections can be varied, thus enabling the neural network to adapt (or learn) in response to training data it receives. In some embodiments, a learning system may be implemented using decision trees. A decision tree is a graph of decisions/actions and their possible outcomes. A decision tree takes as input an object or situation described by a set of properties, and outputs a decision (i.e., an outcome). Alternatively and/or additionally, in some embodiments, the learning system may be implemented using regression techniques. Regression techniques produce functions (e.g., curves) that best fit a given set of data points. That curve is subsequently applied to input data to determine its output based on the derived curve. Derivation of best fit curves are typically the solutions to optimization problems, in which a particular error measure (e.g., least-square error) is being minimized. Other types of learning system implementations may be used.

Figure 4:
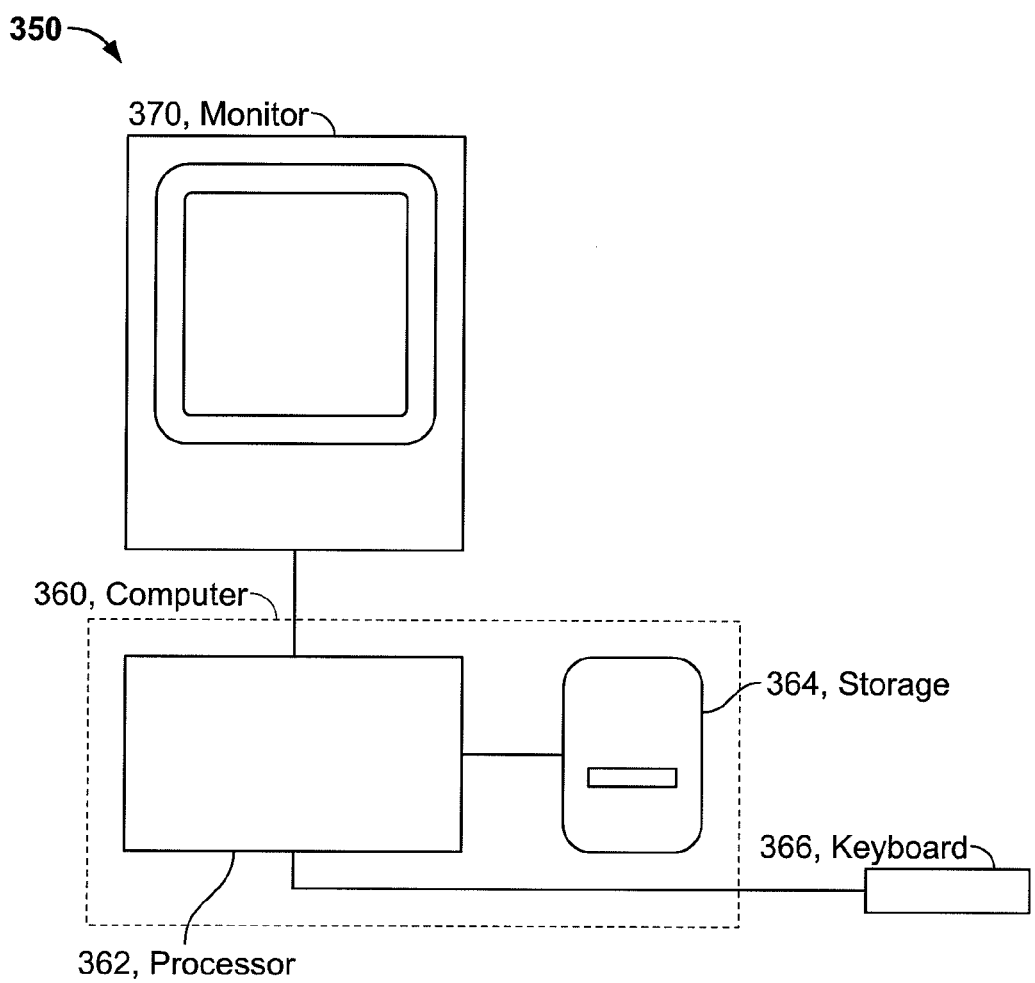
FIG. 4 is a diagram of a generic computing system that can be used with embodiments of the present disclosure.

With reference to FIG. 4, a schematic diagram of a generic computing system 350 that may be used to implement the controller 330 and/or the signal processing unit 320. The computing system 350 includes a processor-based device 360 such as a personal computer, a specialized computing device, and so forth, that typically includes a central processor unit 362. In addition to the CPU 362, the system includes main memory, cache memory and bus interface circuits (not shown). The processor-based device 360 includes a mass storage element 364, which may be the same device or a separate device from storage device 332. The mass storage element 364 may be, for example, a hard drive associated with personal computer systems. The computing system 350 may further include a keyboard 366, a monitor 370, e.g., a CRT (cathode ray tube) or LCD (liquid crystal display) monitor.

The processor-based device 360 is configured to facilitate, for example, the implementation of the data capture and mapping operation used to identify suitable donor sites for harvesting a graft of bone-cartilage as described herein. The storage device 364 may thus include a computer program product that when executed on the processor-based device 360 performs operations to facilitate the implementation of the data capture, mapping and site identification procedures described herein. The processor-based device may further include peripheral devices to enable input/output functionality. Such peripheral devices include, for example, a CD-ROM drive, a flash drive, or a network connection, for downloading related content to the connected system. Such peripheral devices may also be used for downloading software containing computer instructions to enable general operation of the respective system/device, as well as data from remote locations (e.g., donor joint sites data). Alternatively and/or additionally, in some embodiments, special purpose logic circuitry, e.g., an FPGA (field programmable gate array) or an ASIC (application-specific integrated circuit) may be used in the implementation of the system 350. Other modules that may be included with the processor-based device 360 are speakers, a sound card, a pointing device, e.g., a mouse, a trackball or a touch-based GUI, by which the user can provide input to the computing system 350. The processor-based device 360 may include an operating system, e.g., Windows XP® Microsoft Corporation operating system. Alternatively, other operating systems could be used. Additionally or alternatively, one or more of the procedures performed by the processing unit 320 and/or the controller processor 330 may be implemented using processing hardware such as digital signal processors (DSP), field programmable gate arrays (FPGA), mixed-signal integrated circuits, etc.

The various systems and devices constituting the system 300 may be connected using conventional network arrangements. For example, the various systems and devices of system 300 may constitute part of a public (e.g., the Internet) private packet-based network. Other types of network communication protocols may also be used to communicate between the various systems and devices. Alternatively, the systems and devices may each be connected to network gateways that enable communication via a public network such as the Internet. Network communication links between the systems and devices of system 300 may be implemented using wireless or wire-based links. For example, in some embodiments, the controller 330 may include communication apparatus (e.g., an antenna, a satellite transmitter, a transceiver such as a network gateway portal connected to a network, etc.) to transmit and receive data signals. Further, dedicated physical communication links, such as communication trunks may be used. Some of the various systems described herein may be housed on a single processor-based device (e.g., a server) configured to simultaneously execute several applications.

Figure 5:
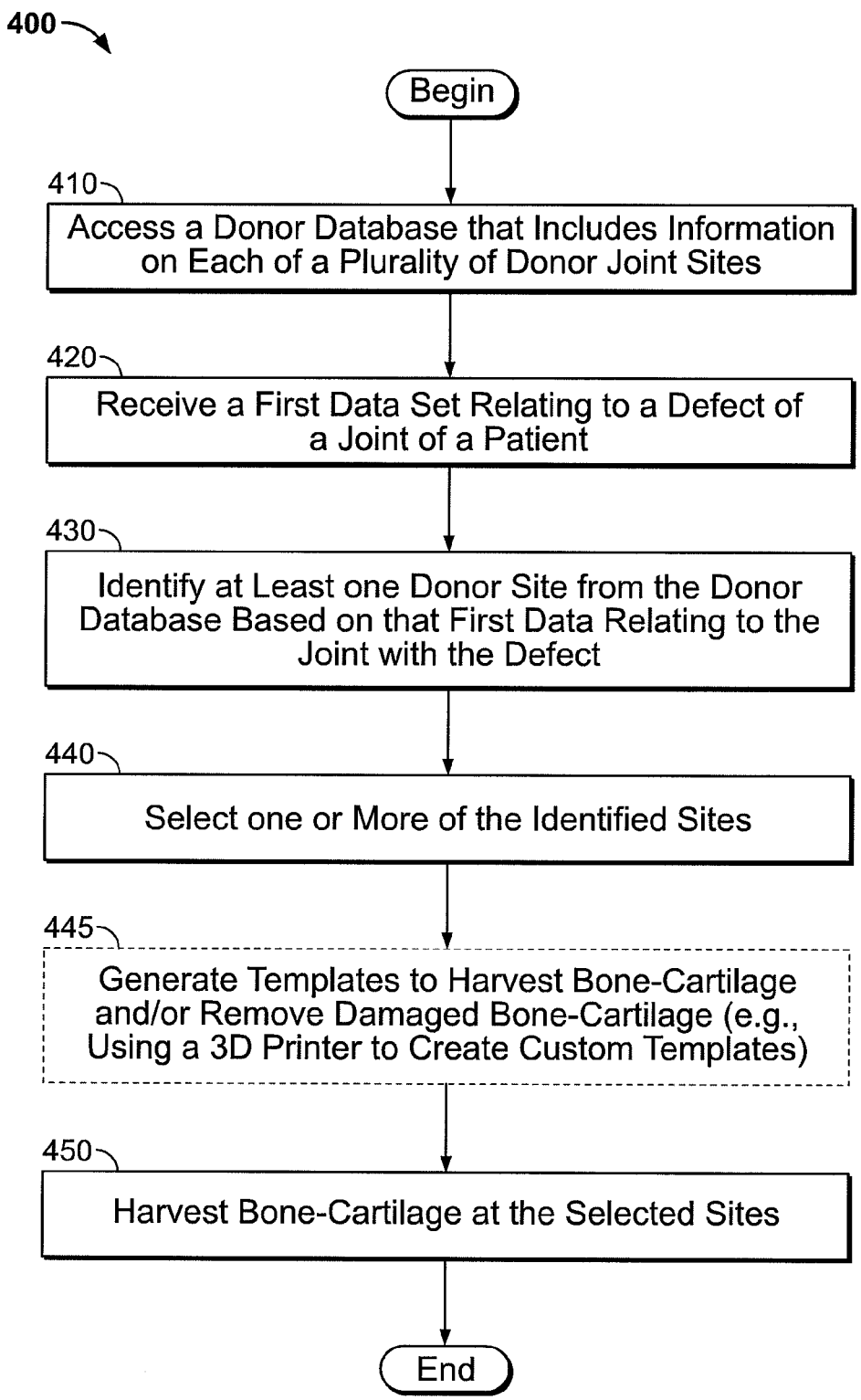
FIG. 5 is a flowchart of a procedure to identify suitable sites for bone-cartilage grafts for repairing a defect in a joint of a patient according to some embodiments of the present disclosure.

Referring to FIG. 5, a flowchart of a procedure 400 to identify suitable sites for bone-cartilage grafts for repairing a defect in a joint of a patient is shown. Initially, a computing device, such as a computer or the controller 330 depicted in FIG. 3 accesses 410 a donor database that includes information on each of a plurality of donor joint sites that may have been compiled and evolved from several sources of data. In some embodiments, the database may have been populated with data downloaded, or otherwise retrieved, from remote locations that maintain data regarding potential donor joint sites. In some embodiments, the data may have been obtained by acquiring raw data, for example, image data obtained using conventional imaging techniques such as MRI imaging, CT imaging, ultrasound imaging, laser scans, etc., from specimens having healthy injured joints (i.e., joints that do not have defects or are otherwise non-injured). For example, in some embodiments, data acquired using a large sample of individuals may be used to assemble data about possible donor joint sites in those individuals, including data representative of the topology, health and other physiological attributes (e.g., gender, age, race, activity index, BMI, $VO_2$, cartilage thickness, bone density, etc.) of those joints. Such data acquired using such a sample of individuals may include data about some or all of feasible sites in a body from which bone and cartilage may be harvested. Accordingly, the individuals used to acquire this data may be put through a comprehensive and systematic protocol of data acquisition procedure such that data regarding all (or substantially all) possible donor sites are acquired. For example, the data acquisition stage required for constructing the database may require that all the joint areas in a person feet be imaged using one or more imaging apparatus and/or surveyed using non-imaging type apparatus (e.g., devices to measure bone density) to obtain a database that accurate and comprehensive. Data processed in this manner is added to the donor database. As noted, in some embodiments, a learning system (e.g., implemented on the controller processor 330 or on some other dedicated processing device) may be used to process acquired data of graft sites (donor sites and/or recipient sites) that is to be added to the database. For example, such a learning system may be used to determine (through implemented classification functions) the identity of the site with respect to which data was received, facilitate the identification procedure to identify donor sites that would be suitable for harvesting bone-cartilage to repair the particular damaged site, etc.

The donor sites with respect to which data is acquired and added to the database include donor sites of different shapes and sizes, including donor sites suitable for harvesting non-cylindrical bone-cartilage grafts. The data for those donor sites can subsequently be used to identify suitable donor sites from which non-cylindrical bone-cartilage grafts can be harvested. Particularly, the systems described herein enable matching irregularly shaped defects of the damaged/injured recipient site(s) to available donor sites that can be used to harvest non-cylindrical bone-cartilage grafts. Conventional bone-cartilage grafting systems and methods typically extract grafts having standard shapes (e.g., cylindrical), thus limiting the repertoire of available donor sites (e.g., donor sites from which such standard shaped grafts can be harvested.) Once suitable donor site are identified, various types of grafts can be harvested, including standard-shaped grafts (e.g., cylindrical grafts) as well as irregularly-shaped grafts. Harvesting irregularly shaped grafts can be performed using a set of pre-determined irregularly shaped templates, or, in some embodiments, by generating custom templates.

Figure 6:
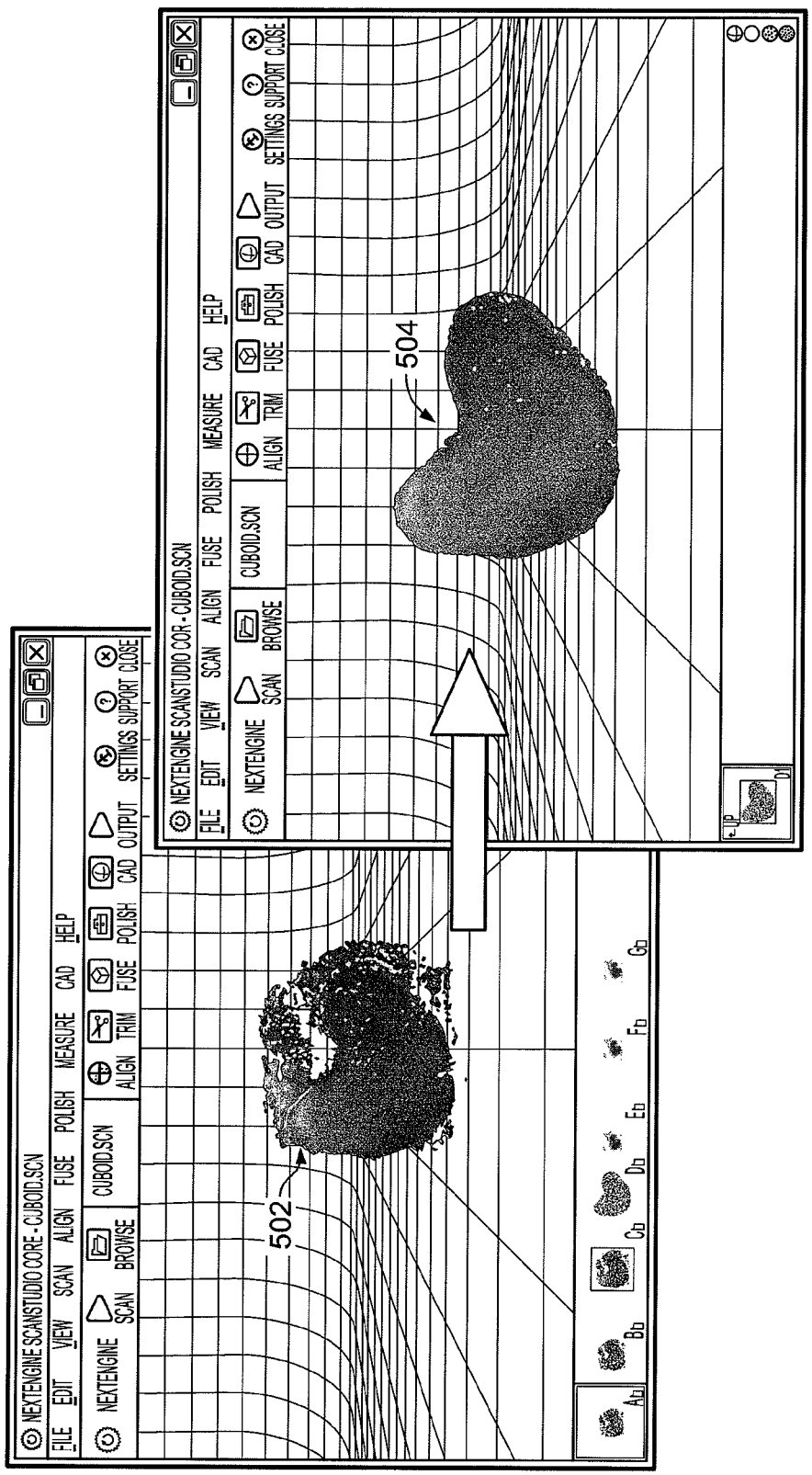
FIG. 6 is a diagram of image data of cuboid cartilage captured using a 400 dpi laser scanner, performed and for use with at least some embodiments of the present disclosure.

In some embodiments, the specimens used to acquire data to populate the donor site database may include cadavers. Under those circumstances, more invasive data acquisition procedures may be used to acquire the data. For example, in some embodiments, one or more of a cadaver's joint may be disarticulated to expose the actual cartilage tissue. With the joint sites of the cadavers disarticulated, a high resolution image scanner may be used to scan the tissue to obtain an accurate representation of the cartilage tissue). A suitable laser scanner to scan exposed cartilage is a NextEngine 3D Scanner, manufactured by NextEngine, Inc. Other laser scanner and/or other types off high quality image capture apparatus may be used. With reference to FIG. 6, a diagram of image data of cuboid cartilage captured using a 400 dpi laser scanner is shown. The acquired raw image data 502 provides a higher quality representation of the cartilage issue than what could be obtained using non-invasive imaging procedures (e.g., MRI or CT imaging).

In some embodiments, data acquired from multiple specimens (be it live individuals or cadavers) may be used to generate a composite representation of donor sites. For example, the data acquired may be averaged to obtain a general representative model of the plurality of donor joint sites. In some variations, several representative models of donor joints and their associated data may be generated from multiple specimens that each correspond to a particular individual type so that, when identification of a suitable donor site is undertaken, a model that is more representative of the particular traits of the patient for whom a bone-cartilage graft is required is used. For example, different general model sets of donor joint sites may be constructed for males and females models.

Figure 7:
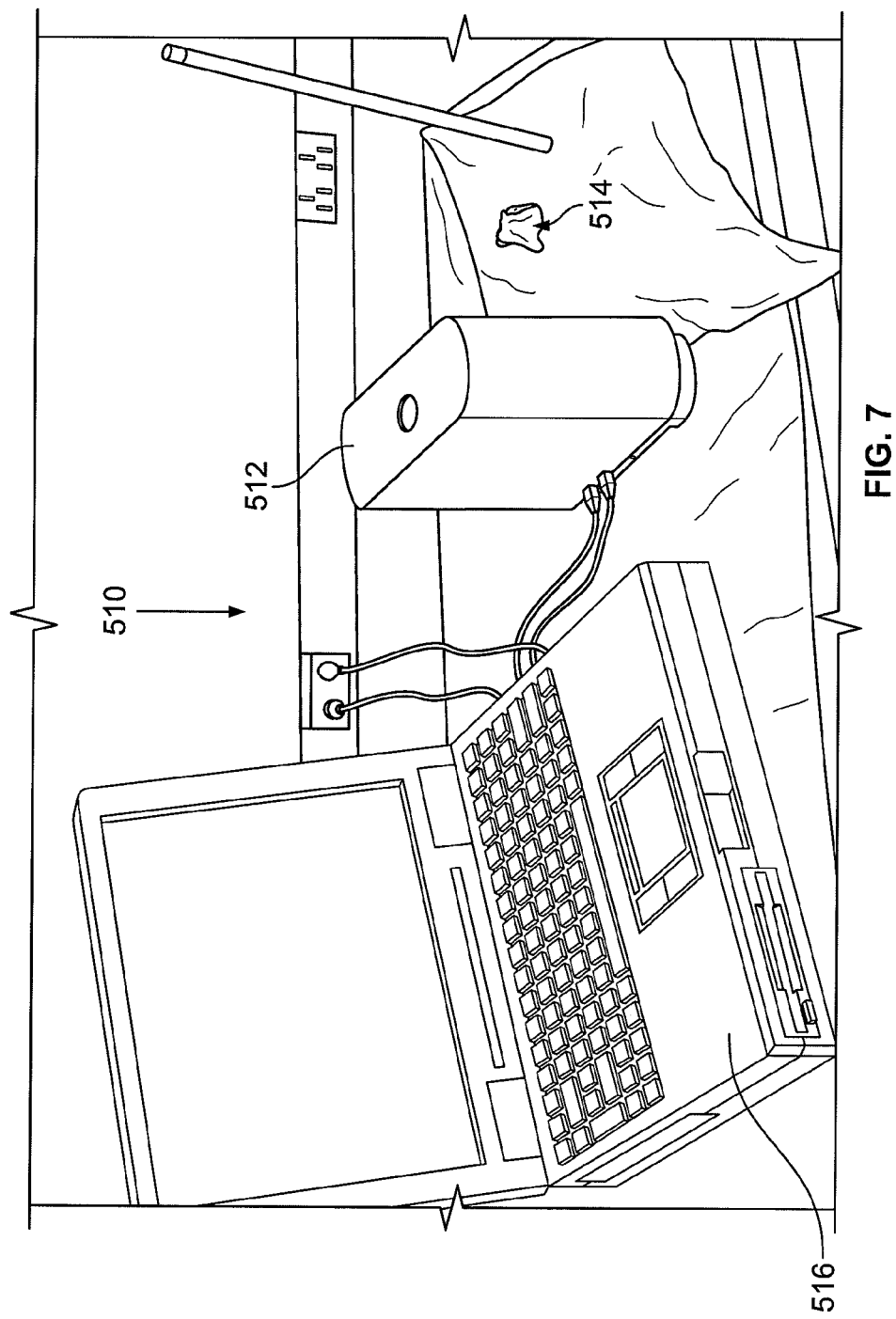
FIG. 7 is a photograph of an example arrangement of a system to acquire, process and store data according to some embodiments of the present disclosure.

In circumstances where the database is constructed, at least partly, by collecting data about body joints (and areas surrounding such joints) from specimens, a system arrangement similar to the arrangement depicted in FIG. 3 may be used. Thus, such an arrangement would include an imaging apparatus such a NextEngine laser scanner to capture data. The captured data would be forwarded to a signal processing apparatus, which may be implemented as a processor-based computing device to perform digital processing (e.g., filtering) on the data and/or a dedicated processing device to perform some or all of the processing operations. A storage device to store captured and/or processed data may also be provided. In some embodiments, such storage device is locally connected to a processor-based computing device which may also serve to perform data processing, perform database management operation (e.g., by executing database management tools), and perform the donor site identification procedure to identify suitable donor sites from which bone-cartilage may be harvested. With reference to FIG. 7, a photograph of an example arrangement of a system 510 to acquire, process and store data is shown. The system 510 includes a laser scanner 512, such as a NextEngine Scanner, whose imaging port (e.g., an outlet through which laser radiation is directed at the object being scanned) is facing an object 514, in this case a disarticulated body joint. Data acquired by the imaging apparatus 512 is communicated to a processing apparatus 516, in this case a computer. The computer 516 typically includes software implemented applications to interface and interact with imaging apparatus 512 and may perform preliminary processing on data communicated by the imaging apparatus, e.g., perform analog-to-digital conversion, down-sample the data, etc. The computer 516 may also be running software-based implementations of data processing applications, for example, SolidWorks 3D CAD software applications. Further, the computer 516 may also include software implementations to perform the donor joint site identification procedure described herein. Data captured and processed may be maintained in a database implemented on the computer 516, or may be stored on a remote storage device and processing center (implemented, for example, on a remote server connected to the computer 516 via a communications network).

Data acquired by imaging apparatus for populating the donor site database may be processed to, for example, remove noisy artifacts from the image, removing unnecessary data, performing various mathematical mapping and transformation operations (e.g., normalization operations, re-sizing/ scaling operations so all data corresponds to features at the same scale, frequency domain transformations, etc.) to transform the data into formats that are more conducive for subsequent search operation on the database (as will be described in greater details below). With reference again to FIG. 6, image data 504 is a resultant processed image of the image data 502 captured by imaging apparatus, in which noise artifacts have been removed.

As noted, further processing on the image data (including image data on which some preliminary processing, including noise filtering and artifact removals has already been performed) is performed on the data to convert it into a format that can subsequently be more easily controlled and is more conducive for performing the joint identification procedure described herein, e.g., use a format that enables comparisons of different joint surfaces to one another. In some implementations, the data acquired is used to generate surface models representative of the joint sites. The surface model may include data regarding the topology of the area, as well as other information descriptive of the area (e.g., bone thickness, bone density).

Several procedures may be used to generate the surface models. For example, in some embodiments, the captured data of the defect is provided as input to various computer aided design (CAD) interface applications, such as, for example, the SolidWorks 3D CAD application developed by Dassault Systèmes SolidWorks Corp., and the application generates a 3D rendering corresponding to the data provided. Specifically, the point cloud of data representative of an acquired image is incorporated into SolidWorks (or any other CAD application used) to generate a resultant surface model. That data can then be stored in a format compatible with the graphical representation rendering, or may be converted and stored using another type of as numerical representations of the surface model features, e.g., be represented as a composite of graphical primitives corresponding, for example, to dimensions and curvatures of lines or segments of the surface model, etc. Referring to FIG. 8, a diagram of a surface model rendering 520 of a cuboid joint is shown. The generated surface model provides topological information of the particular joint and the area surrounding that joint, and may be manipulated to, for example, rotate the surface into different orientations to display different features of the surface that are not necessarily visible in other orientations. As will become apparent below, the generated surface model may be compared with, for example, a surface model representative of the damaged cartilage/bone of a joint, to determine if the potential donor joint would be suitable for harvesting bone-cartilage to repair the defect of the injured joint.

In some embodiments, the generated surface model of the joint may be further manipulated to fit the surface model into a corresponding bone structure to provide further details on the anatomical structure of that potential donor site and provide orientation context to the user on how the surface model is overlaid relative to the bone structure. Referring to FIG. 9, generated 3-D representations 530 and 532, in two different orientations, of the anatomy of the bone, derived from a bone model, and the cartilage surface model, are shown. In some embodiments, the model representation of the bone structure on which the cartilage surface model is overlaid may have been acquired from other specimens (i.e., not necessarily from the same individual whose joint cartilage data was acquired) using imaging apparatus such as MRI imaging apparatus, CT imaging apparatus and/or a laser scanner. Under such circumstances, when a generated surface model of the cartilage is overlaid on a previously acquired or imported model of the bone structure, small anatomical difference between the two models may be evident (e.g., topographical differences, size differences, etc.) Alternatively and/or additionally, in some embodiments, the bone structure models and the joint cartilage models may have been derived from same set of specimens.

Figure 10:
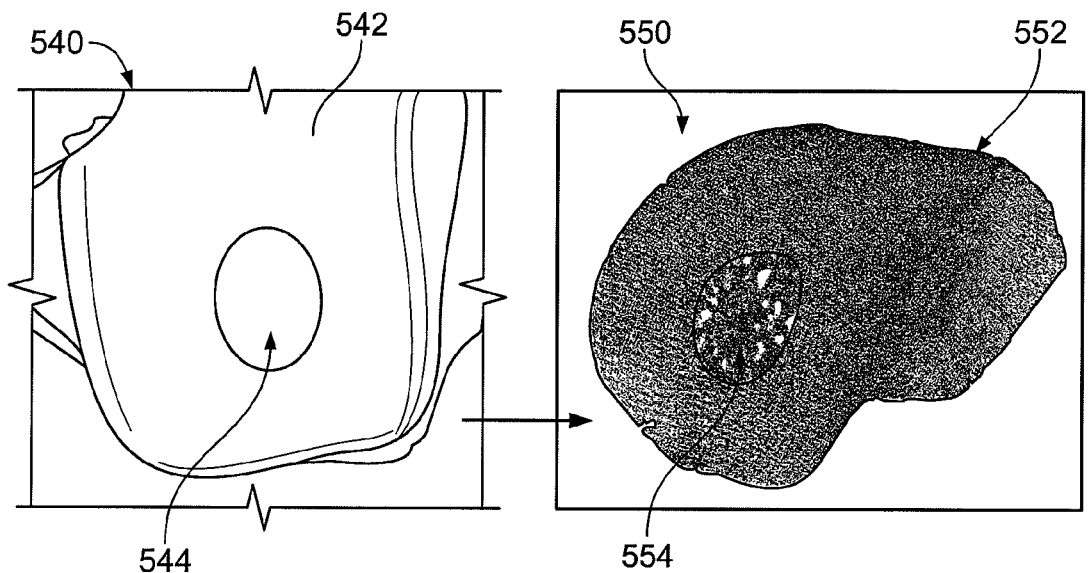
FIG. 10 is an image of a talus joint with a defect, and a resultant surface model of the cartilage of the joint as generated by and for use with at least some embodiments of the present disclosure.

Turning back to FIG. 5, the procedure 400 further includes receiving 420 a first data set relating to a defect of a joint of a patient. As noted, the defect includes an area of a bone, a portion of which includes at least one of a missing and/or damaged cartilage (e.g., hyaline cartilage). In some embodiments, the data relating to the defect may be representative of at least one of, for example, the defect and the area around the defect. As noted, such data may be acquired by using imaging techniques such as MRI, CT, ultrasound, etc., to image the area and construct, using that data, a surface model. The data may have been sent, via a communications link, by a health profession, such as the patient's physician or the surgeon that will perform the graft. The surface model may include data regarding the topology of the area, as well as other information descriptive of the area (e.g., bone thickness, bone density). As noted with respect to the procedure for generating surface models for the potential donor joint sites, there are several procedures that may be used to generate the surface model, including, for example, using the Pro/Engineer CAD application developed by Parametric Technology Corporation, MA, the SolidWorks 3D CAD application developed by Dassault Systèmes SolidWorks Corp., etc., to generate a 3D rendering corresponding to the received first data corresponding to the defect and the area surrounding it. As further noted, the data can then be stored in a format compatible for providing graphical representations of the rendering, or may be converted and stored as numerical representations of the surface model features (e.g., be represented as primitives corresponding, for example, to dimensions and curvatures of lines or segments of the surface model, etc.). FIG. 10 shows an image of an acquired image 540 of a talus joint with a defect, and a resultant surface model of the cartilage of the joint having the defect, generated based on the acquired image 540. In the example shown in FIG. 10, the image 540 may have been acquired, for example, using a CT imaging technique, an MRI imaging technique, and other, generally non-invasive, data acquisition procedures. The bone structure 542 in the image 540 includes a defect 544, indicated using the oval outlines on the image (in this specific example, the defect is a simulated defect, created for the purposes of illustrations of the procedures described herein). Based on the captured data shown in the image 540, a surface model of the cartilage is generated (and possibly also a model for the bone structure) in a manner similar to that used for the surface model and bone structure models populating the donor database. Thus, as shown in the image 550, a surface model 552 of the cartilage is generated from the data representative of the joint with the defect, and includes a corresponding dent-like defect 554 corresponding to the defect appearing in the acquired data of the joint. That surface model 552 may subsequently be manipulated (e.g., rotated, sized, etc.) during the donor site identification procedure to compare the joint with the defect to joint models in the donor database.

In some embodiments, the received data relating to the defect of the joint of the patient is used to identify data in the donor database corresponding to the patient's joint. In other words, instead of using the data relating to the joint with the defect to identify a donor site by comparing the data of the defect to the donor data in the database, the data relating to the joint with the defect is used to first identify a corresponding non-damaged joint structure (i.e., the counterpart healthy joint from the donor database that does not have a defect) which will subsequently be used to identify a suitable donor site to harvest bone-cartilage to repair the joint with the defect.

With continued reference to FIG. 5, once the first data has been received and/or the data was used to generate a surface model to be used in identifying a suitable site or was used to first identify a corresponding healthy joint counterpart from the donor database, at least one donor site from the donor database is identified 430 based on that first data relating to the joint with the defect. Identifying the at least one donor site may include performing comparisons of the data representative of, for example, surface models of donor sites from the database to the first data relating to the joint with the defect, or to some derivative data thereof (for example, a generated surface model for the joint with the defect, a surface model of the same joint but without the defect, or a relevant portion of whichever surface model is selected for performing the comparisons, e.g., only the area in the surface model that includes the defect). Based on those comparisons, the at least one suitable site is determined.

Figure 11:
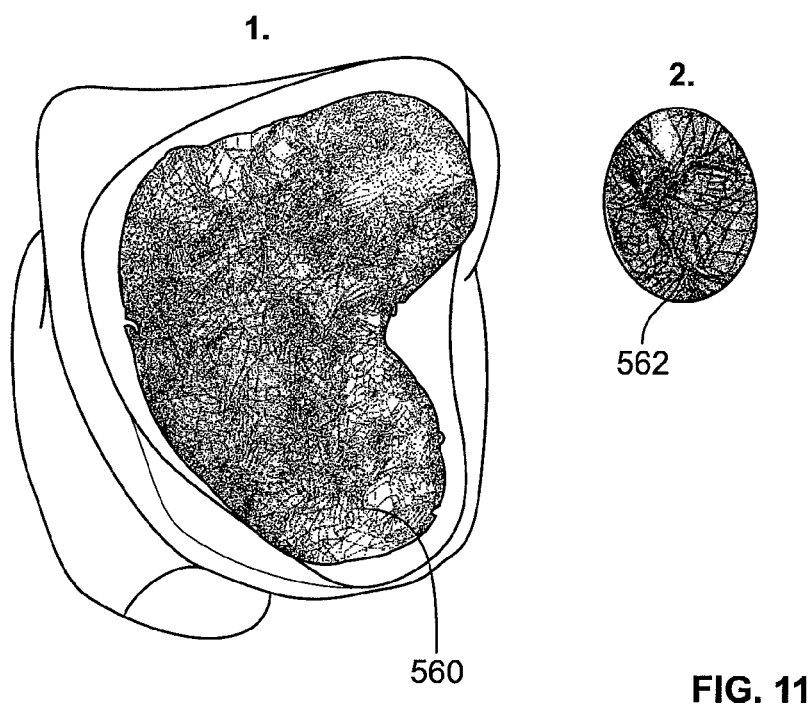
FIG. 11 is a diagram with a portion of a surface model corresponding to a defect in a joint in comparison to a surface model of a cuboid joint as generated by and for use with at least some embodiments of the present disclosure.

More specifically, in some embodiments the surface model data obtained from the data relating to the joint with the defect is used to compare, for example, the dimensions and surface curvatures of the model, to the corresponding dimensions and curvature data of the plurality of donor joint sites in the donor database. With reference to FIG. 11, showing a diagram with a portion 562 of a surface model corresponding to the defect in the joint compared to a surface model 560 of a cuboid joint in the donor database. The two surface models are similarly scaled and directionally tagged to enable an accurate comparison of the two models. The dimensions and curvatures (represented by the meshes on the surface models) can thus be compared to determine if the cuboid joint would be a suitable donor site to harvest bone-cartilage to repair the defect, represented by the surface model 562, in the talus joint in the body of the patient.

Figure 12:
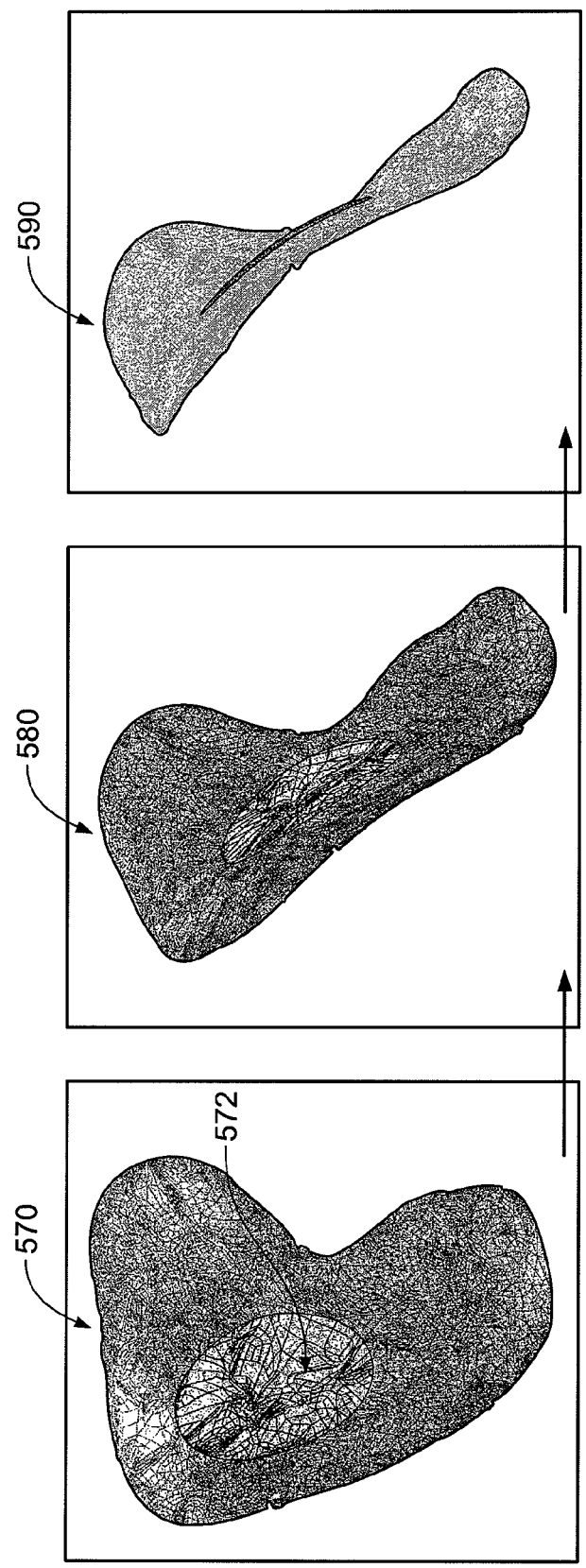
FIG. 12 is a diagram depicting comparisons of a surface model of a defect to a surface model of a cuboid joint as generated by and for use with at least some embodiments of the present disclosure.

In performing the comparisons to identify suitable donor sites the model surfaces can be manipulated to place them in different orientation to facilitate the comparisons. For example, the surface model corresponding to the joint with the defect can be rotated relative to the donor sites surface models to determine optimal matching orientation for the models being compared. For example, the surface model of the joint with the defect is rotated to determine how the curvatures of the surface model match different areas of the surfaces model against which it is compared. Alternatively and/or additionally, in some embodiments, the donor sites surface models are manipulated (e.g., rotated) to compare how those surfaces match the surface model of the joint with the defect in different spatial orientations. The manipulation of the surface models may be performed using the rendering application that was used to generate the surface model, or using a separate application that can perform the manipulation using the rendered models. With reference to FIG. 12, a diagram depicting comparison of a surface model (or a section thereof) to a surface model of a cuboid joint available from the donor database is shown. In image 570, a surface model 572 of the talus joint is compared to a surface model 574 of a potential donor cuboid joint to determine how the two surfaces match at a particular orientation and relative positions of the two surfaces to each other. The results of these comparisons may be expressed using a matching score or metric representative of how well the two surfaces matched at the particular positions and orientation. The level of matching may be based on the extent to which the curvatures and dimensions of the surfaces being compared fit each other (e.g., to what extent are the two surfaces congruent to each other.) Such a determination may be performed, for example, by minimizing the difference between the topologies represented by the two surface models, e.g., finding $\min(\Sigma_{x,y,z} V_{defect(x,y,z)} - V_{donor\ joint(x,y,z)})$, where V represents topology vector values, by minimizing the least-square error of the difference between the surface model representations of the donor and defect sites, etc. In image 580, another orientation and relative positioning of the two surfaces are compared, and here too a matching level score may be obtained to indicate how well the two surfaces fit or match in that relative position and orientation. Image 590 depicts another comparisons performed using a third orientation and relative positioning of the two model surfaces. Here too, a matching level score may be derived. In some embodiments, the optimal matching position orientation of the model surfaces compared may be performed visually by the operator of the system (e.g., a surgeon) who examines the surfaces compared to each other and selects one position/orientation that appears to be one that results in the best match. The procedure of matching the model surface of the joint with the defect to model surfaces of potential donor joint sites is repeated for other joint sites.

To compare the surface model of a defect to one or more donor site surface models, be it through computations based on topological features of the surfaces, or otherwise, the comparison operations may be facilitate by overlaying the surface models against each other. The overlaying operations, for example, the overlaying operations illustrated in FIG. 12, may be achieved using built-in overlaying functions available on the particular graphical rendering application used. For example, when using SolidWorks, the application's alignment functions may be used to position two or more surface model appearing in a view against each other. Alternatively and/or additionally, custom-made procedures for aligning and/or overlaying multiple surface models may be implemented for use with the particular rendering application, or independently of the particular rendering application.

As described herein, the donor database may include donor sites from which irregularly-shaped bone-cartilage grafts (e.g., non-cylindrical grafts) can be harvested. Thus, in situations where the defect has an irregular shape, and the optimal shape of the graft would be one that is substantially similar to the irregular shape of the defect, a surface model of the irregularly-shaped defect, generated in the manner described herein, is used to identify a suitable donor sites from which irregularly-shaped grafts can be harvested. Specifically, the surface model of such an irregularly-shaped defect, which includes small surface segments representative of dimensions and curvatures defining the irregular shape, are compared against one or more donor joint sites stored in the database (with respect to which similar dimension and curvature information is maintained). As described herein, such a comparison may be performed by computing, for example, a minimum of the difference (or the least-square error) between the surface features of the surface models of the defect and surface features of surface model of candidate donor sites. In performing such comparisons the donor surface models and/or the surface model of defect may be re-positioned and have their orientations manipulated to enable comparing surface features of the defect against sub-areas in a particular donor site surface model. In other words, the matching of a defect (e.g., an irregularly-shaped defect) includes, in some embodiments, not only identifying a suitable donor joint site, but also identifying appropriate sub-areas and orientations at the donor site. As also noted herein, in conventional bone-cartilage graft procedures, the grafts generally have standard shapes (e.g., cylindrical), thus limiting the number of possible donor site from which such standard grafts can be harvest, but also making the donor-site identification/matching procedure less complicated because there are fewer donor sites and sub-areas to consider.

In some embodiments, after identifying an appropriate position where the model surface of the defect matches (or reasonably matches) the model surface of the donor site, a cross sectional tool to obtain cross sections of each surface relative to the other may be used. Such a cross-sectional tool may be implemented on the application used to render the models (e.g., Pro/Engineer, SolidWorks 3D), or by using some other application (e.g., some other software implemented tool). Referring to FIG. 13, two different sectional views of the surface models of the defect and a donor site are shown. In image 392 the matched donor site mesh hovers over the recipient site showing congruence of surface texture and contour. In image 394 the corresponding recipient mesh hovers over the donor bone site.

To identify suitable donor sites, comparisons of the surface model corresponding to the damaged joint to surface models from the donor database may be performed according to a hierarchy of matching criteria. Thus, identified suitable donor sites may be ranked to provide a hierarchy of suitable sites from which a user, for example, a surgeon, may select one or more of the listed sites. Examples of matching criteria include the dimensions and/or topological attributes of the joint donor sites, the defect directionality and the area around the defect. In some embodiments, evaluation of the quality of a particular suitable site may be performed in a manner analogous to the matching level score described above, in which the extent of how well the surface of the joint with the defect matches the surface of a potential donor site is determined and a representative "topographical matching" score generated. Another example of a matching criterion is the impact of the harvesting bone-cartilage from a particular donor site will have on the wellbeing of the individual. Particularly, harvesting bone-cartilage from one particular joint may be affect the mobility of the patient (in that the joint may be used, under some circumstances, during movement of the patient), while harvesting bone-cartilage from another joint may have little or no impact on the mobility of the patient (in that that joint is not utilized for mobility). Accordingly, another score (an "impact" score) may be computed to represent the impact of harvesting bone-cartilage from a potential donor joint site. For example, various joints may be associated with pre-determined impact values indicative of the impact harvesting bone-cartilage from that joint would have on a patient's mobility or wellbeing. In some embodiments, a composite score that factors in the various scores derived for a particular joint using the matching criteria may be determined. Such a composite score may be computed, in some embodiments, as a weighted average of the various computed criteria scores for that joint.

Thus, and with reference again to FIG. 5, having identified suitable donor sites from which bone-cartilage can be harvested, and, in some embodiments, having ranked those sites, one or more of the identified sites are selected 440, for example, by a surgeon. Optionally, templates to harvest bone-cartilage and/or remove damaged bone-cartilage may be generated 445. Alternatively, the templates used may be selected from a repertoire of standard, pre-generated templates. Generating custom templates may be based, at least in part, on the received data corresponding to the defect and/or on the data corresponding to the identified donor sites (and/or their associated surface model data) from which bone-cartilage graft(s) to repair the defect will be harvested. In some embodiments, generating custom templates is performed using a 3D printer such as the 3D printer 336 depicted in FIG. 3.

The surgeon may proceed to perform 450 the harvesting procedures at the selected sites. As will be described below in greater details, such procedures may include preparing receiving site and donor site templates, harvesting the bone-cartilage, implanting a processed donor bone-cartilage into the receiving site, etc.

Harvesting and Implanting Bone-Cartilage Graft

To ensure that a grafted healthy articular cartilage follows the contour of surrounding cartilage, the bone and cartilage grafts should be identically shaped. In addition, grafts must be inserted to the proper depth so that the grafted cartilage neither protrudes nor is recessed from the surrounding cartilage. Restoration of normal physiology is achieved through anatomic reconstruction. Accordingly, systems for articular cartilage grafts disclosed herein enable the selection of donor grafts which are shaped to correspond substantially similarly to the defect (and/or the defect as prepared to receive the graft).

The instruments and methods described within the present disclosure achieve these goals. For example, FIGS. 14-17 show various views and diagrams of a specialized set of surgical instruments for harvesting customized, osteochondral and tissue cores from the foot for use in repairing areas of damaged articular cartilage throughout the body, according to some embodiments of the disclosure. Potential sites in the foot that could be used to harvest bone-cartilage include, for example, the calcaneal-cuboid joint, intercuneiform joints, arsometatarsal joints, lesser metatasophalageal joints, interphalangeal joints.

Figure 14:
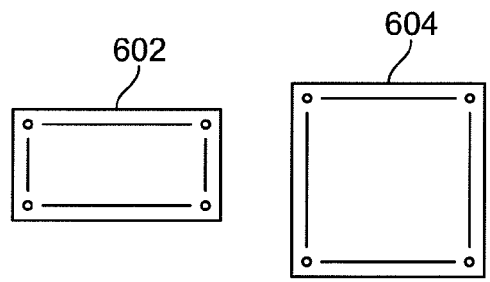
FIG. 14 are schematic diagrams of jigs according to some embodiments of the present disclosure.

A removal jig, such as jigs 602 and 604 shown in FIGS. 14 and 27, may be used to remove raw material blocks (e.g., bone-cartilage-soft-tissue, and the like, also referred to as "bone blocks" or "harvested bone blocks") for larger grafts, which are sculpted into grafts. The removal jig is configured to make precise cuts in the bone, and may be chosen so that the joint from which it removed can be easily fused (for example). The removal jig may be rectangular and may have a contoured surface to match the topography of the defect/recipient site. Accordingly, removal jig is placed on the joint for harvesting and a cutting instrument is used to remove the bone block. For small grafts, a smaller harvester device may be used.

Once the raw material block has been removed, recipient site and donor site templates may be used to create the custom graft and opening for receiving such a graft. In some embodiments, the 3D model generated from image data of the defect (as described above) may then used to create an osteochondral lesion (recipient site) template and a bone block graft (donor site) template, also referred to herein as a negative template and a positive template, respectively. In some embodiments, a two-dimensional topographical data may recreate surface anatomy; conversion to three-dimensional structure may be based upon intraoperative assessment.

Templates may generally be customized, where each template is unique to the defect for repair, or may be partial custom, where one of a limited number of templates can be selected for a particular defect and corresponding donor graft/block. In some embodiments, the templates may be generated based on data (e.g., image data) of the identified donor sites. Such templates may be constructed automatically using a template-making machine that forms the templates based on the data of the identified donor sites. An example of such a template-making machine is a 3D printer, such as the 3D printer 336 depicted in FIG. 3.

Figure 15:
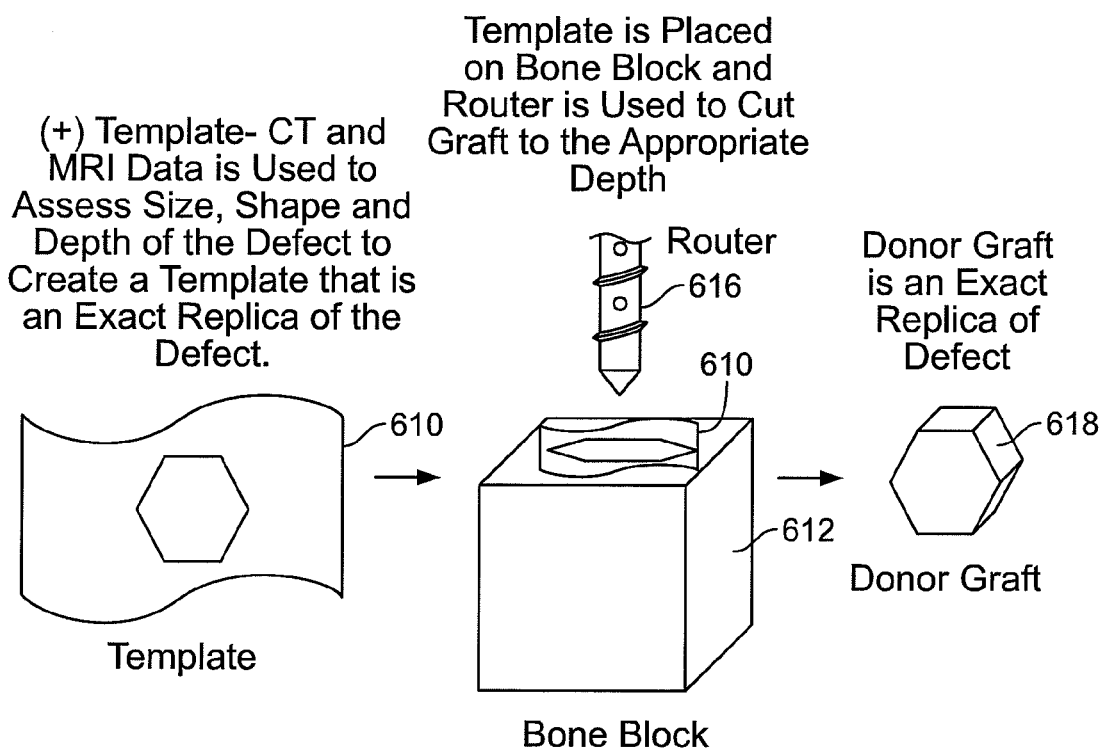
FIG. 15 are diagrams of a positive donor site template placed on a bone block according to some embodiments of the present disclosure.

With reference to FIG. 15, a positive donor site template 610 is placed on bone block 612. Side router 616 is then used to cut around positive template 610 to create custom graft 618, which is a substantially exact match to the size, shape and depth of the defect. Custom graft 618 will then be inserted into the recipient site.

The recipient site and donor grafts produced from a bone block obtained via a removal jig, may be sculpted to obtain their respective desired forms by use of various blades, chisels and router tools individually or in combination (e.g., blade for cartilage preparation and router for bone preparation), familiar to those of skill in the art. Such router tools may include depth setting router bits which attain a predetermined set level of depth, which may be particularly useful when preparing the recipient site, for example. Other tools that may be used include blades for cutting/slicing of cartilage, router for cutting through cortical bone, a recip-saw for sawing through cancellous bone, and a Gigli saw for backside-detachment cut of a raw-material block.

With reference to FIG. 16, a negative recipient site template 622 is placed on recipient site 620. Side router 622 with depth ring 624 (to facilitate controlling the depth of the cut) is used to create the recipient site. Once the recipient site is prepared, donor graft 626 is inserted. It is to be noted that the negative template may also be used, according to some embodiments, as a graft positioning device to facilitate atramatic positioning of the graft within the recipient site.

With reference to FIG. 17, press-fit impaction tool 630 may be used to insert donor graft 632. Press-fit impaction tool 630 may include a swivel and locking universal joint to allow for better control and minimally invasive approaches. In one embodiment, a growth factor may be used in combination with the osteochondral grafts to achieve regeneration and/or functional repair of articular cartilage tissue. The growth factor can be applied directly to the graft and/or implantation site, articulation or whole organism to facilitate restoration of function. Such enhancement may include but would not be limited to, physical, energetic and chemical growth factors, BMPs, stem cells, medications and smart releasing delivery systems.

The active growth factor used in the present disclosure may be from the subclass of proteins known generally as bone morphogenetic proteins (BMPs), which have been disclosed to have osteogenic, chondrogenic and other growth and differentiation type activities. These BMPs include rhBMP-2, rhBMP-3, rhBMP-4 (also referred to as rhBMP-2B), rhBMP-5, rhBMP-6, rhBMP-7 (rhOP-I), rhBMP-8, rhBMP-9, rhBMP-12, rhBMP-13, rhBMP-15, rhBMP-16, rhGDF-10, rhGDF-11, rhGDF-12, rhGDF-14. For example, BMP-2, BMP-3, BMP4, BMP-5, BMP-6 and BMP-7, disclosed in U.S. Pat. Nos. 5,108,922; 5,013,649; 5,116,738; 5,106,748; 5,187,076; and U.S. Pat. No. 5,141,905; BMP-8, disclosed in PCT publication WO91118098; and BMP-9, disclosed in PCT publication WO93100432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in co-pending patent application Ser. No. 081715,202. Other compositions which may also be useful include Vgr-2, and any of the growth and differentiation factors [GDFs], including those described in PCT applications W094115965; W094115949; W095 101 801; W095101802; W094121681; W094115966; W095110539; W09610184.5; W096102559 and others. Also useful in the present disclosure may be BIP, disclosed in W094101557; HP00269, disclosed in JP Publication number: 7-250688; and MP52, disclosed in PCT application WO93 1 16099. The contents of all of these applications/patents/publications are hereby incorporated by reference in their entireties. Also useful in the present disclosure are heterodimers of the above and modified proteins or partial deletion products thereof. These proteins can be used individually or in mixtures of two or more; the protein rh13MP-2 may be used.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-β, super-family, such as activins, inhibins and TGF-β 1 (e.g., a heterodimer composed of one monomer each of a BMP and a related member of the TGF-β superfamily). Examples of such heterodimeric proteins are described for example in Published PCT Patent Application WO 93 109229, the content of which is hereby incorporated by reference in its entirety. The amount of osteogenic protein useful herein is that amount effective to stimulate increased osteogenic activity of infiltrating progenitor cells, and will depend upon the size and nature of the defect being treated, as well as the carrier being employed. Generally, the amount of protein to be delivered is in a range of from about 0.05 to about 1.5 mg.

In some embodiments, the osteogenic protein is administered together with an effective amount of a protein which is able to induce the formation of tendon- or ligament-like tissue. Such proteins include BMP-12, BMP-13, and other members of the BMP-12 subfamily, as well as MP52. These proteins and their use for regeneration of tendon and ligament-like tissue are disclosed in U.S. application Ser. No. 08/362,670, filed on Dec. 22, 1994, (now U.S. Pat. No. 5,658,882), the content of which is hereby incorporated by reference in its entirety. In some embodiments, a heterodimer in which one monomer unit is an osteogenic protein such as BMP-2, and the other monomer subunit is a tendon-inducing protein, such as BMP-12, is administered in accordance with the procedures described herein, in order to induce the formation of a functional attachment between connective tissue and bone.

Growth factor may be applied to the tissue source in the form of a buffer solution. One buffer solution is a composition comprising, in addition to the active growth factor, about 1.0 to about 10.0% (w/v) glycine, about 0.1 to about 5.0% (w/v) of a sugar, e.g., sucrose, about 1 to about 20 mM glutamic acid hydrochloride, and optionally about 0.01 to about 0.1% of a non-ionic surfactant, such as polysorbate 80. Some solutions are from about 1% to about 20% w/v cellulosic carrier/buffer. If desired, a salt may be added.

Other materials which may be suitable for use in application of the growth factors in the methods and compositions of the present disclosure include hyaluronic acid, surgical mesh or sutures, polyglyconate, temperature-sensitive polymers, demineralized bone, minerals and ceramics, such as calcium phosphates, hydroxyapatite, hydrogels etc., as well as combinations of the above described materials. In some embodiments, however, no carrier is employed.

The growth factor which may be used in some embodiments of the present disclosure may be used in a suitable buffer, combined with a suitable carrier, be applied directly to the tissue and/or to the site in need of tissue repair. For example, the growth factor may be physically applied to the tissue through spraying or dipping, or using a brush or some other suitable applicator, such as a syringe for injection. Alternatively, or in conjunction, the protein may be directly applied to the site in need of tissue repair.

Access to a joint to which a defect is being repaired may be accomplished by either one of at least the following three techniques:
1) breaking the bone adjacent the defect/recipient site such that the surgeon can easily access the defect/recipient site;
2) distracting the joint to spread it apart such that the surgeon can easily access the defect/recipient site; and
3) drilling from outside the joint through the bone for which the defect is located such that the surgeon can easily access the defect/recipient site.

Figure 18:
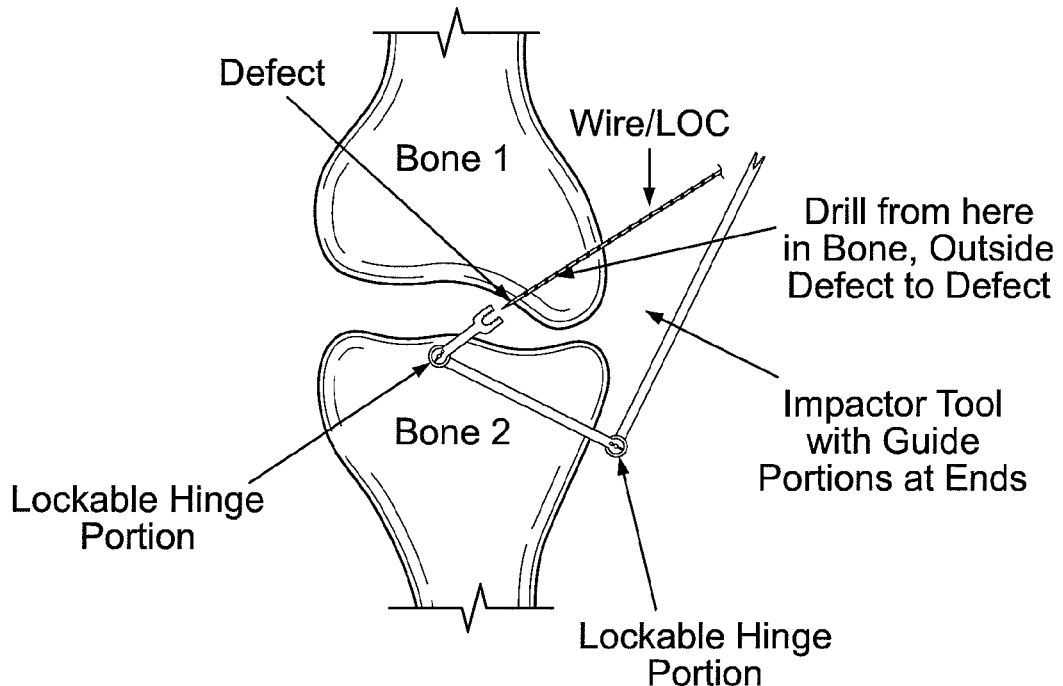
FIG. 18 are diagrams depicting a bone drilling procedure according to some embodiments of the present disclosure.

The third technique for accessing the recipient site may be part of a retrograde approach for placing a donor graft in a recipient site. In a retrograde approach, access to the defect/recipient site is accomplished by drilling from an area of bone located outside and most likely opposed to the defect. The procedure for drilling from an area of the bone located outside and opposite the defect is depicted in FIG. 18.

In some embodiments, an impactor tool with guide portions may be used. A wire/locator may be used which connects one end of the impact tool to the other. The wire may be a threaded compression wire, according to some embodiments of the disclosure, an example of which is shown in FIG. 19.

Figure 19:
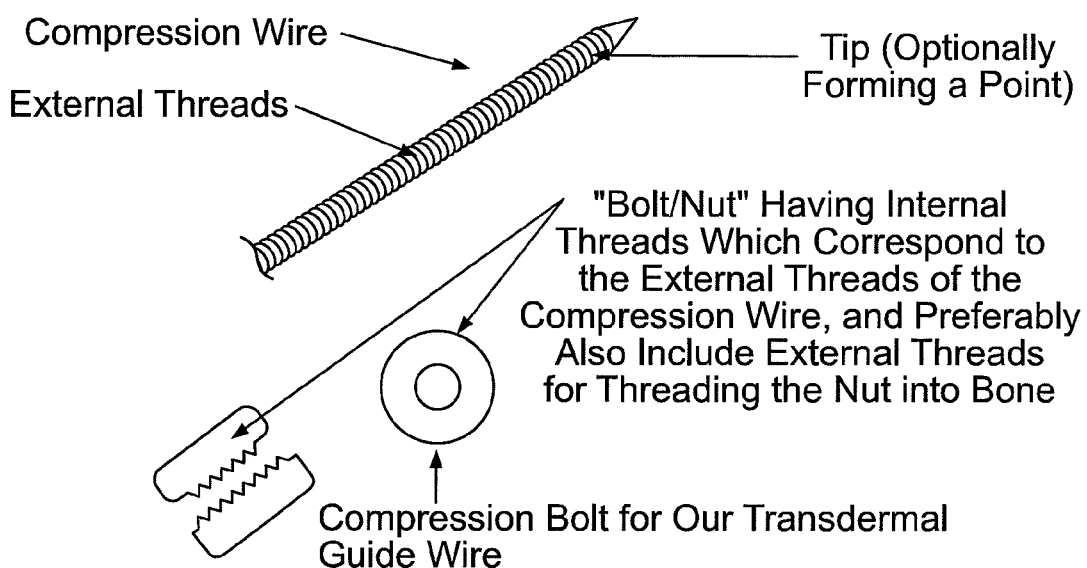
FIG. 19 is a schematic diagram of a compression wire and bolt/nut arrangement according to some embodiments of the present disclosure.

In some embodiments, the threaded compression wire (e.g., such as the one shown in FIG. 19 is configured to provide both rigid internal fixation and controlled variable axial compression in a simple (inexpensive) construct. In some embodiments (as shown), the threaded compression wire includes at least two components, namely, the threaded wire (e.g., similar to a threaded K-wire) and a compressive end bolt/nut.

Embodiments of the threaded compression wire may be used in many procedures, including, for example, surgical correction of an Akin osteotomy. In some embodiments, the compression wire system may be used to provide fixation anywhere a screw, k-wires, staple, suture, wire, plate, rod, bone reconstruction would be used.

Accordingly, in the example of an Akin osteotomy, following the creation of the Akin osteotomy, the treaded wire is secured across the osteotomy in the standard fashion. In some embodiments, the proximal aspect is over drilled to allow for a "sliding compression screw" function to be achieved (for example). The second piece (the compression bolt/nut) may then be applied. The bolt/nut, in some embodiments, includes an internal thread pitch which is the same as the thread pitch on the external threads of the wire. The outer portion/surface of the bolt/nut may have either a conical smooth structure, a flat structure, a variable pitch thread, etc. As the bolt is driven forward on the threads of the wire, compression across the osteotomy site is achieved.

While some embodiments of the threaded compression wire comprise a two part system (including a threaded wire, a threaded compression bolt/nut and a canulated over-drill), other variations are possible. For example, one could utilize a standard threaded Steinman pin/K-wire, but in an effort to reduce cost, the wire could be a threaded bolt and a standard cannulated drill could be used. The compression wire could be a modified smooth pin which deploys end fixation fins to achieve distal fixation, where the proximal bolt/nut would be fixed by either friction on the smooth pin or ratcheting indentations on the smooth pin. In addition, the size of the compression wire could be variable and include an increased in root diameter to account for all currently used screw types.

The threaded compression wire implant as described above enables, in some embodiments, reduced number of surgical steps, thus saving time and effort. The guide pin that is usually placed for a screw may be the actual implant. Moreover, the threaded compression wire implant may secure bony fixation for durability. Furthermore, variable controlled compression by the bolt/nut with various options of fixation through bolt/nut configuration as described above may be provided. The embodiments described herein may also include a bio-absorbable material (either the bolt/nut, the pin/threaded compression wire, or both) for easy elimination of the components upon healing.

The threaded compression wire embodiments described herein not only enable simple and quick fixation, but do not require pre-placement of a guide wire for localization. Rather, it is the threaded compression wire itself that is the actual guide wire. Accordingly, such embodiments would enable a smaller number of operations and instruments, thus decreasing tissue trauma and allowing for a more minimally invasive configuration.

The impaction tool (one embodiments of which is shown above in FIG. 17) may include a tool which, according to some embodiments, includes at least two structural members (e.g., longitudinal portions of stainless steel), which also include a plurality of hinge components to adjust relative angles between the members. The hinges allow guiding ends of the tool to align with one another substantially about 180 degrees apart.

Figure 20:
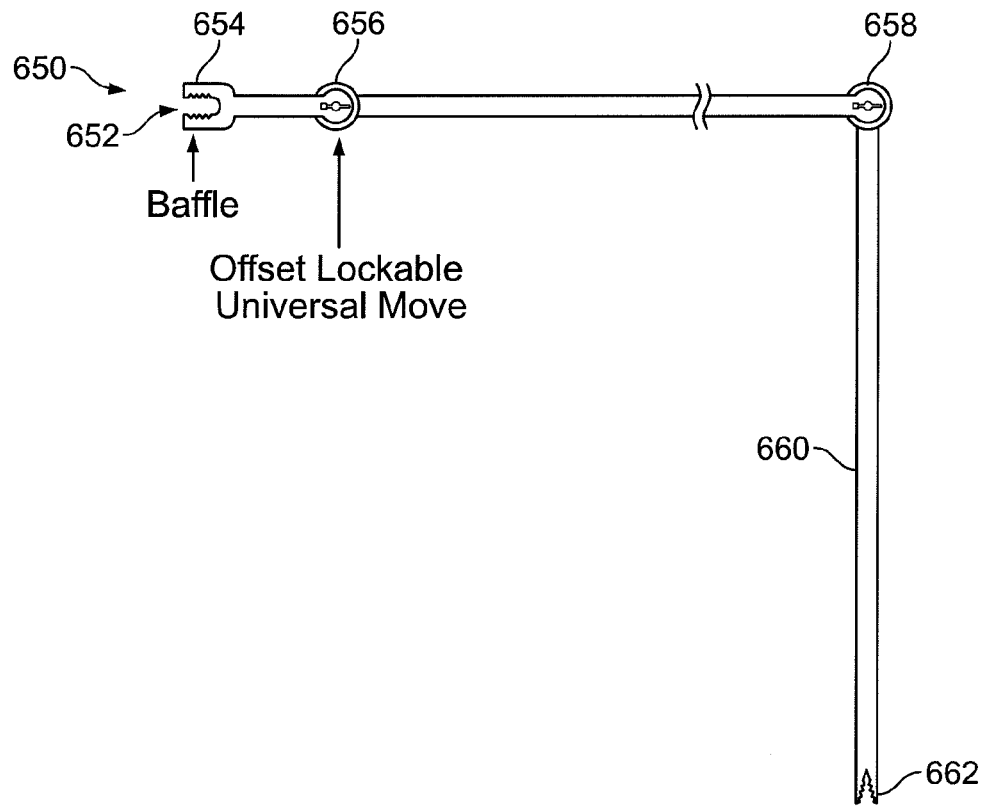
FIG. 20 is a diagram of a targeting, navigating and positioning an impaction tool according to some embodiments of the present disclosure.

For example, and with reference to FIG. 20, in some embodiments, impaction tool 650 comprises a graft connection portion 652 which may include a guide receiving portion 654. Guide receiving portion 654 may comprise an opening, which may be threaded. An offset, lockable hinge 656 is also provided which connects the graft connection portion 652 with another lockable hinge 658. Lockable hinge 658 sits atop a longitudinal structural member 660. On the end opposite to the lockable hinge 658 lies an impaction area, to which a surgeon can apply a force (e.g., via a hammer, mallet, and/or by hand). Adjacent the impaction area, a second guide receiving portion 662 is provided. Guide receiving portion 912 may also comprise an opening which may also be threaded.

At least one of the guide receiving portions, and in some embodiments, at least the guide receiving portion (first guide receiving portion) which is positioned away from the defect (with the other guide receiving portion—second guide receiving portion—positioned adjacent or proximate the defect), includes functionality which enables a surgeon to direct a drill or k-wire substantially straight to the second guide receiving portion. Such functionality may be established by, for example, having a length of tubing which establishes the direction to which the drill or k-wire follows.

The graft connection portion 652 may also include a piece/block of material which is soft (e.g., rubber like material), such that, the material acts as a damper to dampen forces applied to the impactor tool to drive an implant/graft into the recipient site. The material may have a modulus of elasticity approximately equal to that of cartilage.

The multiple hinge portions allow one to adjust the tool such that the guide receiving portions can be adjusted relative to another to allow for alignment with one another (e.g., substantially about 180 degrees apart). As shown in FIG. 18, this allows a surgeon to drill from a position located a distance away from the defect without having to be a substantial distance away (i.e., not having to drill through an axis which lies substantially within the cancellous bone as opposed to an axis through cancellous bone). The angle of approach may then be matched to the offset variable ankle cutting block for graft preparation.

A connector may be provided on any one of the template, graft or graft connection portion, which enables any one of a template or graft to be releasably connected to the graft connection portion 652. Such connectors may be a screw-like connector, an adhesive style connector or other devices which allow for releasable connections.

The lockable hinges may be conventional lockable hinges which may include, for example, a ball and socket joint which utilizes a threaded lock screw to releasably lock the hinge.

One area for which the impaction tool of FIG. 20 (and those similar to it) may be particularly utilized is for any one or more of preparation of a recipient site, as well as positioning of a recipient template and placement of a graft. The tool is particularly useful in such uses, as part of a retrograde approach to placing a graft.

In some embodiments, fixation of a graft may be accomplished by being press-fitted into a recipient site. Specifically, according to some embodiments, the recipient site may be sized to be slightly smaller than the graft, but correspond to it in shape. Thus, the graft can be "pressed" into the recipient site with slight force, and held in place by friction. Other methods of fixating a graft in position may be line-to-line fitting, bone adhesives and/or cements, as well as numerous currently available fasteners.

Figure 21:
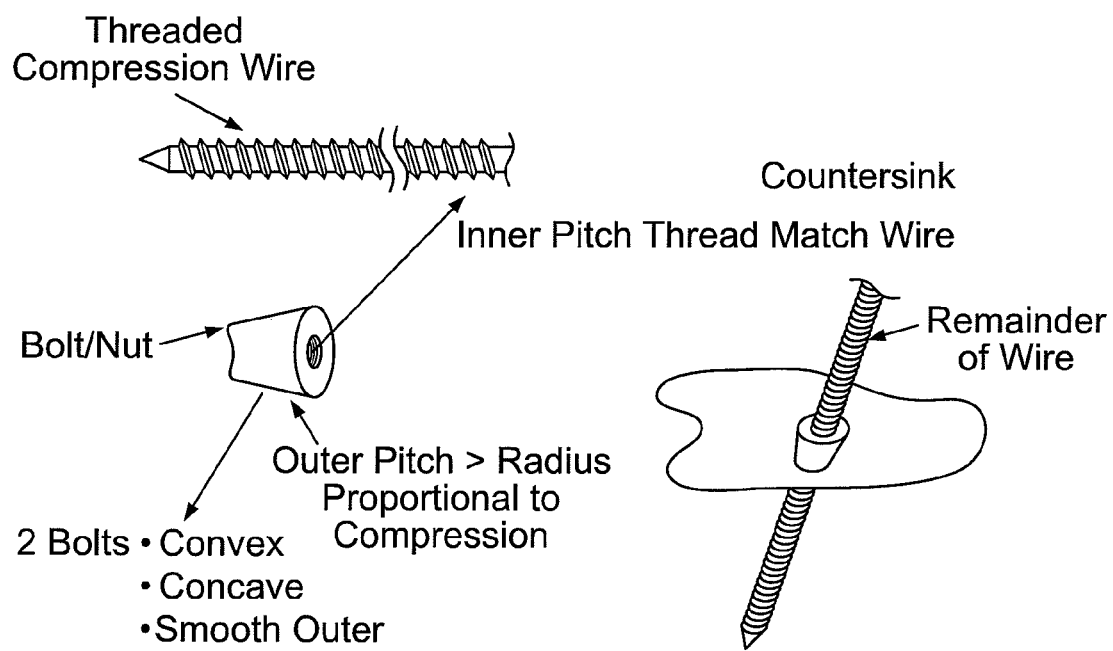
FIG. 21 are diagrams of a compression wire and bolt/nut arrangement in operation according to some embodiments of the present disclosure.

For example, fixation may be effected by use of the threaded compression wire as illustrated in FIG. 19 may be used. In particular, as shown in FIG. 21, the bolt/nut of the threaded compression wire comprise a particular shape, making use of a concave or convex shape (as need be), to allow for a countersunk end.

The bolt/nut includes inner threads which match with the threads of the threaded compression wire, or may include a ratcheting feature so as to allow the threaded compression wire to progressively advance within the bolt/nut. The bolt/nut can be positioned (e.g., threaded or not) into a graft, for example, then receive one end of the threaded compression wire.

Figure 22:
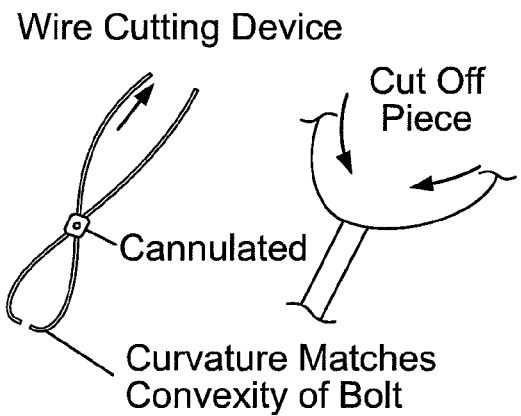
FIG. 22 is a diagram of a cutting tool to cut a compression wire according to some embodiments of the present disclosure.

Once firmly affixed in place, the remainder of the threaded compression wire which sticks out from the bolt/nut (the "remainder" portion shown in FIG. 21) can be cut off in the concave recess of the bolt/nut using a tool like the one illustrated in FIG. 22.

Figure 23:
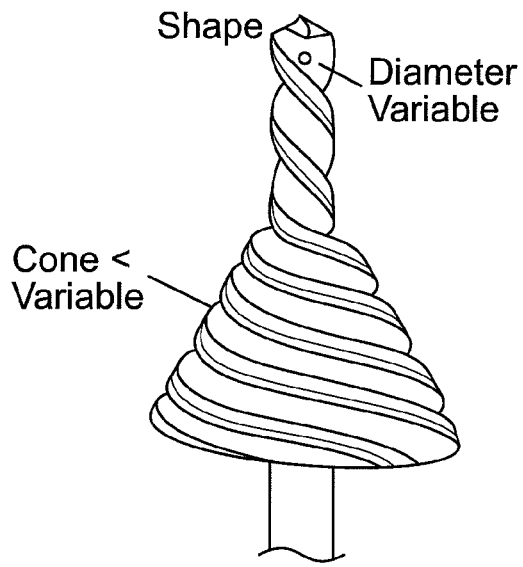
FIG. 23 is a diagram of a drill-bit to prepare an area of a joint defect according to some embodiments of the present disclosure.

Other embodiments of the disclosure include various tools which aid in the system and methods for articular cartilage grafting disclosed herein. For example, for some grafts, a tool may be provided which creates an opening in and around the defect (the recipient site) which corresponds substantially closely to the graft. An example of such a drill bit is shown in FIG. 23.

Figure 24:
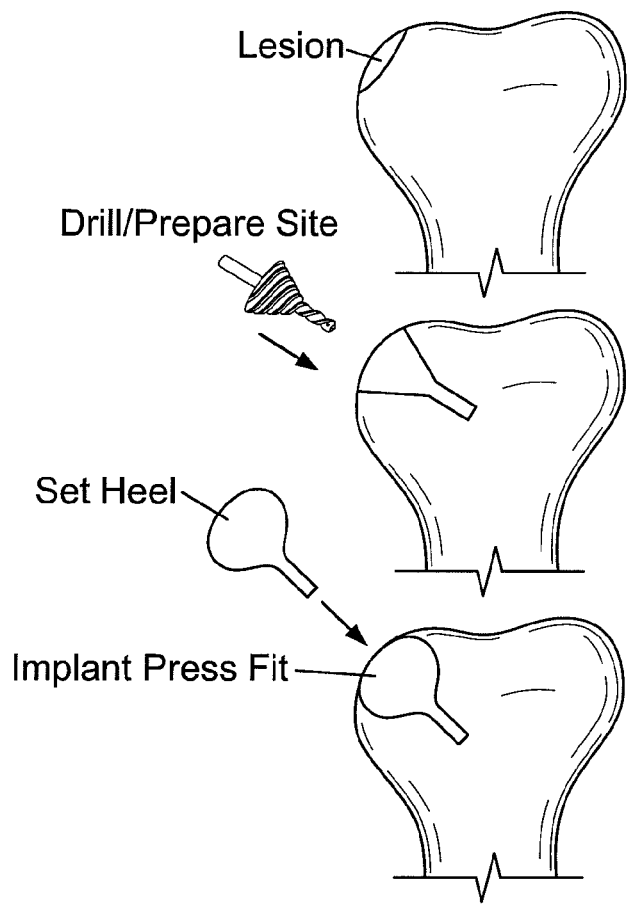
FIG. 24 are diagrams depicting a grafting procedure according to some embodiments of the present disclosure.

As shown, the embodiment of the drill bit may have a variable diameter, and may also include (either separately or together with the variable diameter) a variable cone diameter. In some embodiments, the bit has a proximal shaft diameter identical to that of standard wire/driver surgical tools, thus saving surgical time as the proximal shaft may be grasped rather than mechanically coupled to the drive. Accordingly, such a drill can, in some embodiments, be used in the grafting procedure depicted in FIG. 24.

As described herein, the drill is used to prepare the recipient site where a defect is located, and then a corresponding graft is produced which is substantially similar to the opening created by the drill bit in and around the defect. The graft may be press fitted into the recipient site, and may also be held in place with a bone cement and/or fasteners (e.g., threaded compression wire disclosed herein).

FIGS. 25 and 26 illustrate other examples of articular grafting according to embodiments of the present disclosure.

Other tools that may be used with various embodiments of the disclosure include:

Harvesting/Removal Jigs (an example of which is shown in FIG. 27);
Various saws (examples of which are shown in FIG. 28);
Drill bits and Router bits (examples of which are shown in FIG. 29);
An impactor tool (an example of which is shown in FIG. 30);
Sizing chart (an example of which is shown in FIG. 31); and
Fixation elements (examples of which are shown in FIG. 32).

Other Embodiments

A number of embodiments have been described. Nevertheless, it will be understood that various modifications may be made without departing from the spirit and scope of the invention. Accordingly, other embodiments are within the scope of the following claims.

What is claimed is:

1. A method to identify suitable donor sites for bone-cartilage grafts for repairing a defect in a joint of a patient, the method comprising:
   providing a computer having access to a donor database, the donor database comprising information related to each of a plurality of donor joint sites of the body;
   receiving first data relating to the defect of the joint of the patient, the defect comprising an area of bone, a portion of the defect including at least one of missing and damaged cartilage;
   identifying, using the first data, at least one donor site from the donor database of joints for harvesting a graft of at least one of bone and cartilage to repair the defect; and
   generating a harvesting template using the first data adapted for use at the at least one identified donor site, wherein the harvesting template guides, through physical interaction with a cutting implement, at least one of (i) removal of at least a portion of the defect, and (ii) creation of a graft from the at least one identified donor site.

2. The method of claim 1, wherein the first data comprises imaging data of an area including at least one of the defect and an area around the defect.

3. The method of claim 2, wherein the first data comprises data representative of a surface model of at least one of the defect and the area around the defect.

4. The method of claim 2, wherein the imaging data is captured via at least one of CT imaging, MRI imaging, X-ray imaging and laser imaging.

5. The method of claim 1, wherein receiving the first data comprises accessing from the donor database data representative of a non-damaged structure corresponding to the defect.

6. The method of claim 1, wherein identifying the at least one donor site comprises:
   performing comparisons of data representative of surface models of donor sites retrieved from the donor database to the first data, the first data comprising data representative of a surface model of at least one of the defect and an area around the defect; and determining, using the comparisons, the at least one donor site.

7. The method of claim 6, wherein the comparisons are performed using the surface model of the at least one of the defect and the area around the defect in different spatial orientations.

8. The method of claim 6, wherein performing the comparisons is performed according to a hierarchy of matching criteria.

9. The method of claim 8, wherein the matching criteria include one or more of: a) dimensions of the joint donor sites, the defect and the area around the defect, and b) impact of removal from the respective joint donor sites of one or more of cartilage and bone structure.

10. The method of claim 1, wherein the at least one donor site from the donor database includes at least one foot joint selected from the group consisting of a calcaneal-cuboid joint, intercuneiform joints, arsometatarsal joints, lesser metatasophalageal joints and interphalangeal joints.

11. The method of claim 1, further comprising:
harvesting bone-cartilage from the at least one identified donor site using the generated harvesting template.

12. The method of claim 11, wherein the harvested bone-cartilage has an irregular shape, the irregular shape including a non-cylindrical shape.

13. The method of claim 1, further comprising harvesting a graft of bone and cartilage from an allograft or xenograft source.

14. The method of claim 1, further comprising harvesting a graft of bone and cartilage from a vestigial donor site.

* * * * *